(12) United States Patent
Arora et al.

(10) Patent No.: US 6,380,242 B1
(45) Date of Patent: Apr. 30, 2002

(54) N-ALKYLAMINO-INDOLES FOR THE TREATMENT OF MIGRAINE

(75) Inventors: Jalaj Arora, Cambridge; Louise Edwards, Mississauga; Methvin Isaac, Etobicoke; Anne O'Brien, Toronto; Abdelmalik Slassi; Ashok Tehim, both of Mississauga; Tao Xin, Toronto, all of (CA)

(73) Assignee: NPS Allelix Corp., Ontario (CA)

( * ) Notice: Subject to any disclaimer, the term of this patent is extended or adjusted under 35 U.S.C. 154(b) by 0 days.

(21) Appl. No.: 09/469,327

(22) Filed: Dec. 22, 1999

Related U.S. Application Data

(60) Provisional application No. 60/113,932, filed on Dec. 23, 1998.

(51) Int. Cl.$^7$ .................. A61K 31/382; C07D 409/04; C07D 495/04
(52) U.S. Cl. ................ 514/432; 548/465; 548/504; 549/13
(58) Field of Search ................. 548/465, 466, 548/469, 483, 504; 549/13; 514/432

(56) References Cited

U.S. PATENT DOCUMENTS

| | | | | |
|---|---|---|---|---|
| 4,870,085 A | * | 9/1989 | Glaser et al. ............... | 514/323 |
| 5,182,286 A | * | 1/1993 | Seitz et al. .................. | 514/256 |
| 6,020,336 A | * | 2/2000 | Lavielle et al. ............. | 514/253 |

FOREIGN PATENT DOCUMENTS

| | | | |
|---|---|---|---|
| EP | 0247266 | * | 12/1987 |
| EP | 0287196 | * | 10/1988 |

* cited by examiner

*Primary Examiner*—Alan L. Rotman
*Assistant Examiner*—Rita Desai
(74) *Attorney, Agent, or Firm*—Arent Fox Kintner Plotkin & Kahn PLLC

(57) ABSTRACT

The present invention is directed to compounds useful in the treatment of migraine which have the general formula (II).

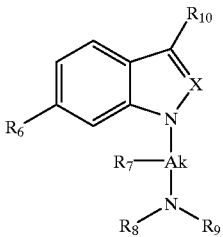

8 Claims, No Drawings

N-ALKYLAMINO-INDOLES FOR THE TREATMENT OF MIGRAINE

This application claims the benefit of U.S. Provisional Application No. 60/113,932, filed Dec. 23, 1998.

FIELD OF THE INVENTION

This invention relates to the use of certain indole and indazole derivatives in the treatment of migraine. Further, the invention relates to certain N-alkylamino indole and indazole compounds, to pharmaceutical and diagnostic compositions containing them and to their medical use, particularly in the treatment or diagnosis of CNS conditions.

BACKGROUND OF THE INVENTION

Through its interaction with receptors found on neuronal and other cells, 5-hydroxytryptamine (5-HT or serotonin) mediates a variety of physiological effects. Imbalances in this interaction are believed to be responsible for such conditions as anxiety, hallucination, migraine, chemotherapy-induced nausea and for disorders in sexual activity, cardiovascular activity and thermoregulation, amongst others. From an improved understanding of the 5-HT receptor population it is apparent that these effects are mediated selectively through individual types and subtypes of the 5-HT receptors. Migraine, for example, has been treated with ergotamine, dihydroergotamine, methylsergide and, most recently, sumatriptan, all of which presumably act at the 5-HT$_{1D}$ receptor subtype.

Current treatments for migraine, including sumatriptan, continue to have unwanted side effects. These include coronary vasospasm, hypertension and angina. Recent evidence suggests that the observed sumatriptan-mediated contraction of coronary arteries may be due to the stimulation of the 5-HT$_{1B}$ (formerly 5-HT$_{1D\beta}$) subtype of the 5-HT receptors (Kaumann, A. J. Circulation, 1994, 90:1141–1153).

Given the physiological and clinical significance of the 5-HT$_{1D}$ receptor, and the potential side effect liability of stimulation of the 5-HT$_{1B}$ receptor, it would be desirable to provide compounds that bind with high affinity to the 5-HT$_{1D}$ receptor. Such compounds would be medically useful, for example, to treat indications for which administration of a 5-HT$_{1D}$ ligand is indicated, such as migraine. Such compounds could also be used diagnostically, for example, to identify these receptors and to screen drug candidates.

SUMMARY OF THE INVENTION

It has been found that compounds of Formula I,

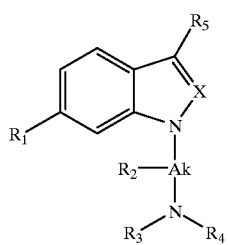

I wherein:
X is selected from the group consisting of N, CH and C-lower alkyl;
R$_1$ represents a 5 to 7-membered monocyclic or benzo-fused heterocyclic ring, which may be unsaturated, and which may contain one or more substituents selected from the group consisting of lower alkyl, hydroxy, lower alkoxy, amino and mono- or di-lower alkyl amino;
Ak represents a C$_{1-3}$alkylene chain which may be substituted with R$_2$, where R$_2$ represents lower alkyl;
R$_3$ and R$_4$ are independently selected from the group consisting of H, lower alkyl, lower alkenyl, cycloalkyl and optionally-substituted benzyl; or one pair of R$_2$ and R$_3$ or R$_3$ and R$_4$ together may form an alkylene or alkenylene bridge which, with the nitrogen atom, form a 3- to 7-membered ring which may contain one or more substituents selected from the group consisting of lower alkyl, hydroxy, hydroxymethyl, alkoxymethyl, amino and substituted amino;
R$_5$ is selected from the group consisting of H, lower alkyl and a 4- to 7-membered carbocyclic or heterocyclic group, which may be unsaturated
and salts and solvates thereof, bind to the Serotonin 5-HT$_{1D}$ receptor and are, therefore, useful, in accordance with one aspect of the invention, for the treatment of diseases such as migraine.

In another aspect of the invention, compounds of Formula I, and radio-labeled forms thereof, are also useful as a pharmacological tool for the identification of other compounds, including potential drug candidates, which bind to the 5-HT$_{1D}$ receptor.

Radio-labeled forms of compounds of Formula I are also useful as diagnostic tools for the identification of 5-HT$_{1D}$ binding sites in vitro.

According to another aspect of the present invention there are provided compounds of Formula II and a salt, solvate or hydrate thereof:

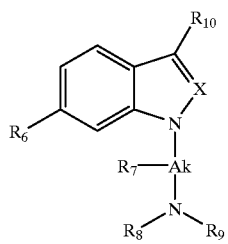

II wherein:
X is selected from the group consisting of N, CH and C-lower alkyl;
R$_6$ represents a 5 to 7-membered monocyclic or benzo-fused heterocyclic ring, which may be unsaturated, and which may contain one or more substituents selected from the group consisting of lower alkyl, hydroxy, lower alkoxy, amino and mono- or di-lower alkyl amino;
Ak represents a C$_{1-3}$alkylene chain which may be substituted with R$_7$, where R$_7$ represents lower alkyl;
R$_8$ and R$_9$ are independently selected from the group consisting of H, lower alkyl, lower alkenyl, cycloalkyl and optionally-substituted benzyl;
R$_{10}$ is selected from the group consisting of H, lower alkyl and a 4- to 7-membered carbocyclic or heterocyclic group, which may be unsaturated.

It is another aspect of the present invention to provide compounds which bind selectively to the 5-HT$_{1D}$ receptor, relative particularly to the 5-HT$_{1B}$ receptor.

According to another aspect of the invention there are provided compositions comprising a compound of Formula I and a carrier, either for use as reagents, for example in the identification of 5-HT$_{1D}$ receptors or 5-HT$_{1D}$ receptor ligands, or for pharmaceutical use to treat conditions where stimulation of the 5-HT$_{1D}$ receptor is indicated.

According to another aspect of the invention there are provided compositions comprising a compound of Formula II and a carrier.

It is another aspect of the present invention to provide a method effective to treat medical conditions for which stimulation of the 5-HT$_{1D}$ receptor is indicated, such as migraine.

These and other aspects of the present invention are described in greater detail hereinbelow.

DETAILED DESCRIPTION OF THE PREFERRED EMBODIMENTS

The term "lower alkyl" as used herein means straight and branched chain alkyl radicals containing from one to six carbon atoms and includes methyl, ethyl, propyl, isopropyl, t-butyl and the like.

The term "cycloalkyl" as used herein means a 3- to 7-membered carbocyclic ring and includes cyclopropyl, cyclohexyl and the like.

The term "lower alkoxy" as used herein means straight and branched chain alkoxy radicals containing from one to six carbon atoms and includes methoxy, ethoxy, propyloxy, isopropyloxy, t-butoxy and the like.

The term "optionally substituted benzyl" as used herein means an unsubstituted benzyl radical or a benzyl radical substituted on the phenyl ring with 1–3 substituents independently selected from halo, OH, $C_{1-6}$alkyl, $C_{1-6}$alkoxy, $C_{1-6}$alkylthio, $CF_3$ and $CF_3O$.

The term "pharmaceutically acceptable salt" means an acid addition salt which is compatible with the treatment of patients.

A "pharmaceutically acceptable acid addition salt" is any non-toxic organic or inorganic acid addition salt of the base compounds represented by Formula I or any of their intermediates. Illustrative inorganic acids which form suitable salts include hydrochloric, hydrobromic, sulfuric and phosphoric acids, as well as acid metal salts such as sodium monohydrogen orthophosphate and potassium hydrogen sulfate. Illustrative organic acids which form suitable salts include mono-, di- and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluenesulfonic and methanesulfonic acids. Either the mono- or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used, for example, in the isolation of compounds of Formula I for laboratory use, or for subsequent conversion to a pharmaceutically acceptable acid addition salt.

The term "solvate" means a compound of Formula I, or a pharmaceutically acceptable salt of a compound of Formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a hydrate.

The term "stereoisomers" is a general term for all isomers of a molecule which differ only in the orientation of their atoms in space. It includes image isomers (enantiomers), geometric (cis/trans) isomers and isomers of compounds with more than one chiral centre which are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The present invention includes within its scope prodrugs of the compounds of Formula I. In general, such prodrugs will be functional derivatives of a compound of Formula I which are readily convertible in vivo into the compound from which it is notionally derived. Conventional procedures for the selection and preparation of suitable prodrug derivatives are described, for example, in "Design of Prodrugs" ed. H. Bundgaard, Elsevier, 1985.

Compounds of Formula I bind to the serotonin 5-HT$_{1D}$ receptor. Preferred compounds of Formula I bind selectively (for example with 10-fold selectivity) to the serotonin 5-HT$_{1D}$ receptor, relative, particularly, to the serotonin 5-HT$_{1B}$ receptor, as judged by in vitro binding affinities using, for example, the assay exemplified herein. More preferred compounds are those which bind with at least 10-fold selectivity to the 5-HT$_{1D}$ receptor, relative to the 5-HT$_{1B}$ receptor. Most preferred are those compounds which bind with at least 40-fold selectivity to the 5-HT$_{1D}$ receptor, relative to the 5-HT$_{1B}$ receptor.

Some of the compounds of Formula II may have at least one asymmetric centre. Where the compounds according to the invention have one asymmetric centre they may exist as enantiomers. Where the compounds according to the invention possess two or more asymmetric centres, they may additionally exist as diastereomers. It is to be understood that all such isomers and mixtures thereof in any proportion are encompassed within the scope of the present invention.

Acid addition salts of the compounds of Formula II are most suitably formed with pharmaceutically acceptable acids, and include, for example, those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used, for example, in the isolation of compounds of Formula I for laboratory use, or for subsequent conversion to a pharmaceutically acceptable acid addition salt.

The conversion of a given compound salt to a desired compound salt is achieved by standard techniques in which an aqueous solution of the given salt is treated with a solution of base e.g. sodium carbonate, potassium hydroxide to liberate the neutral compound which is then extracted into an appropriate solvent, such as ether. The neutral compound is then separated from the aqueous portion, dried, and treated with the requisite acid to give the desired salt.

Also included within the scope of the invention are solvates of the compounds of the invention. The formation of a solvate will vary depending on the compound and solvent used. In general, solvates are formed by dissolving the compound in the appropriate solvent and isolating the solvate by cooling or using an antisolvent. The solvate is typically dried or azeotroped under ambient conditions.

Prodrugs of compounds of the invention may be conventional esters formed with available hydroxyl (or thiol) or carboxyl groups. For example, when one of $R^3$ or $R^4$ in a compound of Formula I contains an OH group, it may be acylated using an activated acid in the presence of a base and, optionally, in inert solvent (e.g. an acid chloride in pyridine). Some common esters which have been utilized as prodrugs are phenyl esters, aliphatic ($C_1$–$C_{24}$) esters, acyloxymethyl esters, carbamates and amino acid esters.

Compounds of Formula I include those in which $R_1$ is a monocyclic or benzo-fused heterocyclic ring. Preferably, $R_1$ is a monocyclic ring (such as pyridinyl or thienyl). More preferably $R_1$ is a non-aromatic ring (such as piperidinyl, pyranyl or thiopyranyl), and may contain a hydroxy substituent. Most preferably, the ring is unsubstituted. In general, heterocyclic rings containing O or S are preferred over N-containing rings.

The alkylene chain Ak is preferably unsubstituted, and is, more preferably, a 2-carbon chain.

$R_3$ and $R_4$ are, preferably, independently selected small groups such as methyl, ethyl, cyclopropyl and the like. More preferably, $R_3$ and $R_4$ are methyl, most preferably one of $R_3$ or $R_4$ is methyl and the other is H.

$R_5$ is, preferably, H or lower alkyl, more preferably H or Me and, most preferably, $R_5$ is H.

The novel compounds of Formula II, which form another aspect of the invention, follow, broadly, the SAR outlined above for the compounds of Formula I (that is, the preferred compounds follow the same trend).

Specific compounds useful in the treatment of migraine include:

(R)-1-((N-Methylpyrrolidin-2-yl)methyl)-6-(3-pyridinyl)-1H-indole;
(R)-1-((N-Methylpyrrolidin-2-yl)methyl)-6-(3-thienyl)-1H-indole;
(R)-1-(2-(N-(2-Hydroxymethyl)pyrrolidinyl)ethyl)-6-(3-thienyl)-1H-indazole;
(R)-1-(N-Methylpyrrolidin-2-yl)methyl)-6-(1-methyl-1,2,5,6-tetrahydro-4-pyridine)-1H-indole;
(R)-1-(N-Methylpyrrolidin-2-yl)methyl)-6-(3-thienyl)-1H-indazole;
(R)-1-(Pyrrolidin-2-yl)methyl)-6-(3-thienyl)-1H-indazole;
(R)-6-(4-Hydroxy-N-methylpiperidin-4-yl)-1-(N-methylpyrrolidin-2-yl)methyl)-1H-indole;
(R)-6-(N-Methylpiperidin-4-yl)-1-(N-methylpyrrolidin-2-yl)methyl)-1H-indole;
(R,S)-1-(2-(N,N-Dimethylamino)propyl)-6-(1-methyl-1,2,5,6-tetrahydro-4-pyridine)-1H-indole;
(R,S)-1-(2-(N,N-Dimethylamino)propyl)-6-(3-pyridinyl)-1H-indole;
(R,S)-1-(2-(N,N-Dimethylamino)propyl)-6-(3-thienyl)-1H-indole;
(S)-1-((N-Methylpyrrolidin-2-yl)methyl)-6-(3-pyridinyl)1H-indole;
(S)-1-((N-Methylpyrrolidin-2-yl)methyl)-6-(2-thienyl-1H-indole;
(S)-1-(2-(N-(2-Hydroxymethyl)pyrrolidinyl)ethyl)-6-(3-thienyl)-1H-indazole;
1-(2-(1-Azetidinyl)ethyl)-6-(3-thienyl)-1H-indazole;
1-(2-(N-(1-Benzylpyrrolidin-3-yl)amino)ethyl)-6-(3-thienyl)-1H-indazole;
1-(2-(N-(3-Hydroxypyrrolidinyl)ethyl))-6-(3-thienyl)-1H-indazole;
1-(2-(N,N-Diethylamino)ethyl)-6-(1-tert-butoxycarbonyl-pyrrol-2-yl)-1H-indazole;
1-(2-(N,N-Diethylamino)ethyl)-6-(2,3-dihydrothiopyran-4-yl)-1H-indole;
1-(2-(N,N-Diethylamino)ethyl)-6-(3-pyridinyl)-1H-indole;
1-(2-(N,N-Diethylamino)ethyl)-6-(3-thiophene)-1H-indole;
1-(2-(N,N-Diethylamino)ethyl)-6-(4-hudroxy-tetrahydrothiopyran-4-yl)-1H-indole;
1-(2-(N,N-Diethylamino)ethyl)-6-(4-methyl-2-thienyl)-1H-indazole;
1-(2-(N,N-Diethylamino)ethyl)-6-(5-chloro2-thienyl)-1H-indazole;
1-(2-(N,N-Diethylamino)ethyl)-6-(5-methyl-2-thienyl)-1H-indazole;
6-(Benzo[b]thien-2-yl)-1-(2-(N,N-diethylamino)ethyl)-1H-indazole;
6-(Benzo[b]furan-2-yl)-1-(2-(N,N-diethylamino)ethyl)-1H-indazole;
1-(2-(N,N-Diethylamino)ethyl)-6-(furan-3-yl)-1H-indazole;
1-(2-(N,N-Diethylamino)ethyl)-6-(N-methyltetrahydro-4-pyridinyl)-1H-indazole;
1-(2-(N,N-Diethylamino)ethyl)-6-(3-pyridinyl)-1H-indazole;
1-(2-(N,N-Diethylamino)ethyl)-6-(tetrahydropyran-4-yl)-1H-indazole;
1-(2-(N,N-Diethylamino)ethyl)-6-(tetrahydrothiopyran-4-yl)-1H-indazole;
1-(2-(N,N-Diethylamino)ethyl)-6-(tetrahydrothiopyran-4-yl)-1H-indole;
1-(2-(N,N-Diethylamino)ethyl)-6-(3-thienyl)-1H-indazole;
1-(2-(N,N-Dimethylamino)ethyl)-6-(1-methyl-1,2,5,6-tetrahydro-4-pyridine)-1H-indazole;
1-(2-(N,N-Dimethylamino)ethyl)-6-(4-hydroxy-tetrahydrothiopyran-4-yl)-1H-indole;
6-(6H-2,3-Dihydrothiopyran-4-yl)1-(2-(N,N-dimethylamino)ethyl)-1H-indole;
6-(Benzo[b]thiophene-2-yl)-1-(2-(N,N-dimethylamino)ethyl)-1H-indole;
1-(2-(N,N-Dimethylamino)ethyl)-6-(N-methyl-2,3-dihydro-4-piperidinyl)-1H-indole;
1-(2-(N,N-Dimethylamino)ethyl)-6-(N-methyl-4-hydroxy-4-piperidinyl)-1H-indole;
1-(2-(N,N-Dimethylamino)ethyl)-6-(N-methylpiperidin-4-yl)-1H-indazole;
1-(2-(N,N-Dimethylamino)ethyl)-6-(N-methyl-piperidin-4-yl)-1H-indole;
1-(2-(N,N-Dimethylamino)ethyl)-6-(pyridin-2-yl)-1H-indole;
1-(2-(N,N-Dimethylamino)ethyl)-6-(3-pyridinyl)-1H-indazole;
1-(2-(N,N-Dimethylamino)ethyl)-6-(3-pyridinyl)-1H-indole;
1-(2-(N,N-Dimethylamino)ethyl)-6-(4-pyridinyl)-1H-indazole;
1-(2-(N,N-Dimethylamino)ethyl)-6-(tetrahydropyran-4-yl)-1H-indazole;

1-(2-(N,N-Dimethylamino)ethyl)-6-(tetrahydrothiopyran-4-yl)-1H-indole;
1-(2-(N,N-Dimethylamino)ethyl)-6-(2-thienyl)-1H-indazole;
1-(2-(N,N-Dimethylamino)ethyl)-6-(2-thienyl)-1H-indole;
1-(2-(N,N-Dimethylamino)ethyl)6-(3-thienyl)-1H-indazole;
1-(2-(N,N-Dimethylamino)ethyl)-6-(3-thienyl)-1H-indole;
1-(2-(N,N-Dipropylamino)ethyl)-6-(3-thienyl)-1H-indazole;
1-(2-(N-Allylamino)ethyl)-6-(3-thienyl)-1H-indazole;
1-(2-(N-Benzylamino)ethyl)-6-(3-thienyl)-1H-indazole;
1-(2-(N-Cyclopropylamino)ethyl)-6-(3-thienyl)-1H-indazole;
1-(2-(N-Cyclopropylmethylamino)ethyl)-6-(3-thienyl)-1H-indazole;
1-(2-(N-Isopropylamino)ethyl)-6-(3-thienyl)-1H-indazole,
1-(2-(N-Methylamino)ethyl)-6-(3-thienyl)-1H-indazole;
1-(2-(N-Piperidinyl)ethyl)-6-(3-thienyl)-1H-indazole;
1-(2-(N-Propylamino)ethyl)-6-(3-thienyl)-1H-indazole;
1-(2-(N-Pyrrolidinyl)ethyl)-6-(3-thienyl)-1H-indazole;
1-(2-(N-Pyrrolin-3-yl)ethyl)-6-(3-thienyl)-1H-indazole;
6-(2,3-Dihydropyran-4-yl)-1-(2-(pyrrolidinyl)ethyl-1H-indole;
6-(4-Hydroxy-tetrahydropyran-4-yl)-1-(2-(pyrrolidinyl)ethyl-1H-indole;
1-(2-(Pyrrolidinyl)ethyl-6-(tetrahydropyran-4-yl)-1H-indole;
6-(3-Pyridinyl)-1-(2-pyrrolidinyl)ethyl-1H-indole;
1-(3-(N,N-Diethylamino)propyl)-6-(3-thienyl)-1H-indazole;
1-(3-(N,N-Dimethylamino)propyl)-6-(3-pyridinyl)-1H-indole;
1-(3-(N,N-Dimethylamino)propyl)-6-(4-hydroxy-tetrahydrothiopyran-4-yl)-1H-indole;
6-(6H-2,3-Dihydrothiopyran-4-yl)-1-(3-(N,N-dimethylamino)propyl)-1H-indole;
1-(3-(N,N-Dimethylamino)propyl)-6-(tetrahydrothiopyran-4-yl)-1H-indole;
1-(3-(N,N-Dimethylamino)propyl)-6-(3-thienyl-1H-indazole;
1-(3-(N-Pyrrolin-3-yl)propyl)-6-(3-thienyl)-1H-indazole;
1-(3-N,N-Dimethylamino)propyl-6-(2-thiophene)-1H-indole
1-(N-Cyclopropylamino)ethyl)-6-(4-hydroxy-tetrahydrothiopyran-4-yl)-1H-indole;
1-(N-Cyclopropylamino)ethyl-6-(2,3-dihydrothiopyran-4-yl)-1H-indole;
1-(N-Methyl-azepan-3-yl)-6-(3-thienyl)-1H-indole;
1-(N-Methyl piperidin-2-yl)methyl)-6-(3-thienyl)-1H-indole;
3-(1-Cyclohexenyl)-1-(2-(N,N-dimethylamino)ethyl)-6-(3-Pyridyl)-1H-indole;
3-(1-Cyclohexyl)-1-(2-(N,N-dimethylamino)ethyl)-6-(3-Pyridyl)-1H-indole;
6-(3-Aminopyrrolidin-1-yl)-1-((N,N-dimethylamino)ethyl)-1H-indole;
1-(2-(N,N-Dimethylamino)ethyl)-6-(4-hydroxy-tetrahydropyran-4-yl)-1H-indole;
6-(6H-2,3-Dihydropyran-4-yl)-1-(2-(N,N-dimethylamino)ethyl)-1H-indole;
1-((N,N-Dimethylamino)ethyl)-6-(N-morpholinyl)-1H-indazole;
1-((N,N-Dimethylamino)ethyl)-6-(N-morpholinyl)-1H-indole;
1-((N,N-Dimethylamino)ethyl)-6-(N-thiomorpholinyl)-1H-indole and
1-(2-(N,N-Dimethylamino)ethyl)-6-(tetrahydropyran-4-yl)-1H-indole.

Preferred embodiments of the invention include:
(R)-1-((N-Methylpyrrolidin-2-yl)methyl)-6-(3-pyridinyl)-1H-indole;
(R)-1-((N-Methylpyrrolidin-2-yl)methyl)-6-(3-thienyl)-1H-indole;
(R)-1-(2-(N-(2-Hydroxymethyl)pyrrolidinyl)ethyl)-6-(3-thienyl)-1H-indazole;
(R)-1-(N-Methylpyrrolidin-2-yl)methyl)-6-(3-thienyl)-1H-indazole;
(R)-1-(Pyrrolidin-2-yl)methyl)-6-(3-thienyl)-1H-indazole;
(R,S)-1-(2-(N,N-Dimethylamino)propyl)-6-(3-pyridinyl)-1H-indole;
(R,S)-1-(2-(N,N-Dimethylamino)propyl)-6-(3-thienyl)-1H-indole;
(S)-1-((N-Methylpyrrolidin-2-yl)methyl)-6-(2-thienyl)-1H-indole;
(S)-1-((N-Methylpyrrolidin-2-yl)methyl)-6-(3-pyridinyl)1H-indole;
(S)-1-(2-(N-(2-Hydroxymethyl)pyrrolidinyl)ethyl)-6-(3-thienyl)-1H-indazole;
1-(2-(1-Azetidinyl)ethyl)-6-(3-thienyl)-1H-indazole;
1-(2-(N-(1-Benzylpyrrolidin-3-yl)amino)ethyl)-6-(3-thienyl)-1H-indazole;
1-(2-(N-(3-Hydroxypyrrolidinyl)ethyl))-6-(3-thienyl)-1H-indazole;
1-(2-(N-(3-tert-Butoxycarbonylamino)pyrrolidinyl)ethyl)-6-(3-thienyl)-1H-indazole;
1-(2-(N,N-Diethylamino)ethyl)-6-(3-furanyl)-1H-indazole;
1-(2-(N,N-Diethylamino)ethyl)-6-(3-pyridinyl)-1H-indazole;
1-(2-(N,N-Diethylamino)ethyl)-6-(3-pyridinyl)-1H-indole;
1-(2-(N,N-Diethylamino)ethyl)-6-(3-thienyl)-1H-indazole;
1-(2-(N,N-Diethylamino)ethyl)-6-(3-thienyl)-1H-indole;
1-(2-(N,N-Diethylamino)ethyl)-6-(4-methyl-2-thienyl)-1H-indazole;
1-(2-(N,N-Diethylamino)ethyl)-6-(5-methyl-2-thienyl)-1H-indazole;
1-(2-(N,N-Dimethylamino)ethyl)-6-(2-pyridinyl)-1H-indole;
1-(2-(N,N-Dimethylamino)ethyl)-6-(2-thienyl)-1H-indazole;
1-(2-(N,N-Dimethylamino)ethyl)-6-(2-thienyl)-1H-indole;
1-(2-(N,N-Dimethylamino)ethyl)-6-(3-pyridinyl)-1H-indazole;
1-(2-(N,N-Dimethylamino)ethyl)-6-(3-pyridinyl)-1H-indole;
1-(2-(N,N-Dimethylamino)ethyl)-6-(3-thienyl)-1H-indazole;
1-(2-(N,N-Dimethylamino)ethyl)-6-(3-thienyl)-1H-indole;
1-(2-(N,N-Dimethylamino)ethyl)-6-(4-pyridinyl)-1H-indazole;

1-(2-(N,N-Dipropylamino)ethyl)-6-(3-thienyl)-1H-indazole;
1-(2-(N-Allylamino)ethyl)-6-(3-thienyl)-1H-indazole;
1-(2-(N-Benzylamino)ethyl)-6-(3-thienyl)-1H-indazole;
1-(2-(N-Cyclopropylamino)ethyl)-6-(3-thienyl)-1H-indazole;
1-(2-(N-Cyclopropylmethylamino)ethyl)-6-(3-thienyl)-1H-indazole;
1-(2-(N-Isopropylamino)ethyl)-6-(3-thienyl-1H-indazole,
1-(2-(N-Methylamino)ethyl)-6-(3-thienyl)-1H-indazole;
1-(2-(N-Piperidinyl)ethyl)-6-(3-thienyl)-1H-indazole;
1-(2-(N-Propylamino)ethyl)-6-(3-thienyl)-1H-indazole;
1-(2-(N-Pyrrolidinyl)ethyl)-6-(3-thienyl)-1H-indazole;
1-(2-(N-Pyrrolin-3-yl)ethyl)-6-(3-thienyl)-1H-indazole;
1-(3-(N,N-Diethylamino)propyl)-6-(3-thienyl)-1H-indazole;
1-(3-(N,N-Dimethylamino)propyl)-6-(3-pyridinyl)-1H-indole;
1-(3-(N,N-Dimethylamino)propyl)-6-(3-thienyl)-1H-indazole;
1-(3-(N-Pyrrolin-3-yl)propyl)-6-(3-thienyl)-1H-indazole;
1-(3-N,N-Dimethylamino)propyl-6-(2-thienyl)-1H-indole
1-(N-Methyl-3-azepinyl)-6-(3-thienyl)-1H-indole;
1-(N-Methylpiperidin-2-yl)methyl)-6-(3-thienyl)-1H-indole;
3-(1-Cyclohexenyl)-1-(2-(N,N-dimethylamino)ethyl)-6-(3-pyridyl)-1H-indole;
3-(1-Cyclohexyl)-1-(2-(N,N-dimethylamino)ethyl)-6-(3-pyridyl)-1H-indole;
6-(3-Pyridinyl)-1-(2-pyrrolidinyl)ethyl-H-indole;
6-(5-Chloro-2-thienyl)-1-(2-(N,N-diethylamino)ethyl)-1H-indazole; and
6-(Benzo[b]-2-thienyl)-1-(2-(N,N-diethylamino)ethyl)-1H-indazole.

More preferred embodiments of the invention include:
(R)-1-(N-Methylpyrrolidin-2-yl)methyl)-6-(1-methyl-1,2,5,6-tetrahydro-4-pyridinyl)-1H-indole;
(R)-6-(4-Hydroxy-N-methyl-4-piperidinyl)-1-(N-methyl-2-pyrrolidinyl)methyl)-1H-indole;
(R)-6-(N-Methyl-4-piperidinyl)-1-(N-methyl-2-pyrrolidinyl)methyl)-1H-indole;
(R,S)-1-(2-(N,N-Dimethylamino)propyl)-6-(1-methyl-1,2,5,6-tetrahydro-4-pyridinyl)-1H-indole;
1-((N-Cyclopropylamino)ethyl)-6-(2,3-dihydrothiopyran-4-yl)-1H-indole;
1-(2-(N,N-Diethylamino)ethyl)-6-(2,3-dihydrothiopyran-4-yl)-1H-indole;
1-(2-(N,N-Diethylamino)ethyl)-6-(4-hydroxy-tetrahydrothiopyran-4-yl)-1H-indole;
1-(2-(N,N-Diethylamino)ethyl)-6-(N-methyltetrahydro-4-pyridinyl)-1H-indazole;
1-(2-(N,N-Diethylamino)ethyl)-6-(tetrahydropyran-4-yl)-1H-indazole;
1-(2-(N,N-Diethylamino)ethyl)-6-(tetrahydrothiopyran-4-yl)-1H-indazole;
1-(2-(N,N-Diethylamino)ethyl)-6-(tetrahydrothiopyran-4-yl)-1H-indole;
1-(2-(N,N-Dimethylamino)ethyl)-6-(1-methyl-1,2,5,6-tetrahydro-4-pyridinyl)-1H-indazole;
1-(2-(N,N-Dimethylamino)ethyl)-6-(4-hydroxy-tetrahydropyran-4-yl)-1H-indole;
1-(2-(N,N-Dimethylamino)ethyl)-6-(4-hydroxy-tetrahydrothiopyran-4-yl)-1H-indole;
1-(2-(N,N-Dimethylamino)ethyl)-6-(N-methyl-2,3-dihydro-4-piperidinyl)-1H-indole;
1-(2-(N,N-Dimethylamino)ethyl)-6-(N-methyl-4-hydroxy-4-piperidinyl-1H-indole;
1-(2-(N,N-Dimethylamino)ethyl)-6-(N-methyl-4-piperidinyl)-1H-indazole;
1-(2-(N,N-Dimethylamino)ethyl)-6-(N-methyl-4-piperidinyl)-1H-indole;
1-(2-(N,N-Dimethylamino)ethyl)-6-(tetrahydropyran-4-yl)-1H-indazole
1-(2-(N,N-Dimethylamino)ethyl)-6-(tetrahydropyran-4-yl)-1H-indole;
1-(2-(N,N-Dimethylamino)ethyl)-6-(tetrahydrothiopyran-4-yl)-1H-indole;
1-(2-(Pyrrolidinyl)ethyl)-6-(tetrahydropyran-4-yl)-1H-indole;
1-(N-Cyclopropylamino)ethyl)-6-(4-hydroxy-tetrahydrothiopyran-4-yl)-1H-indole;
6-(2,3-Dihydropyran-4-yl)-1-((2-pyrrolidinyl)ethyl)-1H-indole;
6-(3-Amino-1-pyrrolidinyl)-1-((N,N-dimethylamino)ethyl)-1H-indole;
6-(4-Hydroxy-tetrahydropyran-4-yl)-1-(2-(pyrrolidinyl)ethyl)-1H-indole;
6-(6H-2,3-Dihydropyran-4-yl)-1-(2-(N,N-dimethylamino)ethyl)-1H-indole; and
6-(6H-2,3-Dihydrothiopyran-4-yl)-1-(2-(N,N-dimethylamino)ethyl)-1H-indole.

In accordance with another aspect of the invention, the compounds of the invention can be prepared by processes analogous to those established in the art.

For example, compounds of Formula I where $R_1$ is a non-aromatic group can be prepared as shown below in Scheme 1.

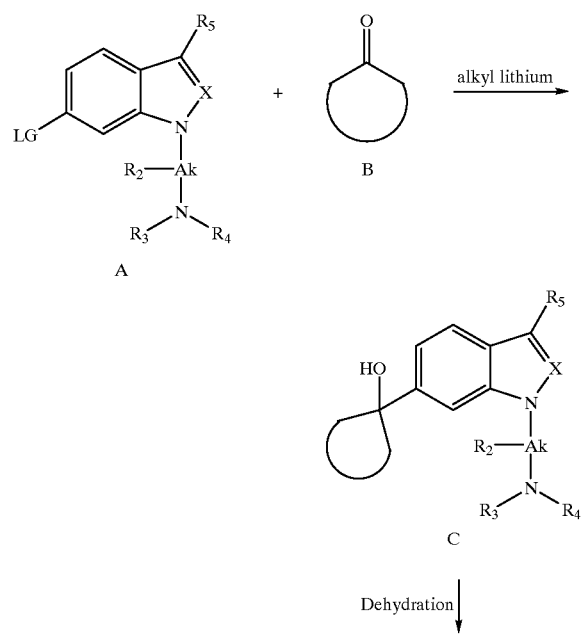

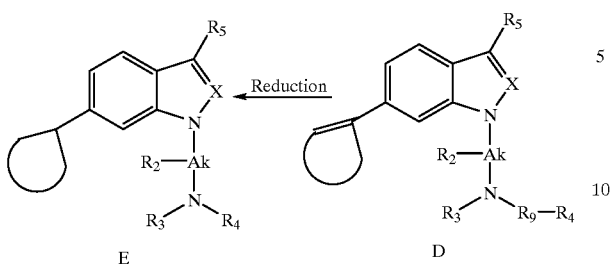

E ← Reduction ← D

Intermediate A, wherein LG is a group which undergoes lithium exchange (such as halo, preferably bromo or iodo), when treated with an alkyllithium such as n- or t-butyllithium, followed by the addition of a cyclic ketone of Formula B to provide compounds of Formula C. This reaction is performed in inert solvents, such as ether or tetrahydrofuran, at temperatures ranging from −100 to 0° C. Preferred conditions are tetrahydrofuran at −78° C. Compounds of Formula C may be dehydrated under standard conditions, for example, by formation of the mesylate and elimination under basic conditions or, alternatively, in the presence of an acid such as trifluoroacetic acid in an inert solvent such as tetrahydrofuran, to provide compounds of Formula D. Compounds of formula D can be reduced, for example by treatment with hydrogen in the presence of a catalyst, such as palladium on charcoal, to give saturated compounds E.

Compounds of Formula I can also be prepared by direct treatment of intermediate A with the appropriate boronic acid (or ester or diester of boronic acid, as shown in scheme 2) under basic conditions, in the presence of a catalyst such as tetrakis(triphenylphosphine) palladium (0). The 6-substituent can also be introduced by treatment of intermediate A with $R_1SnBu_3$ (for example) in THF, again in the presence of a catalytic amount of tetrakis (triphenylphosphine) palladium (0).

Scheme 2

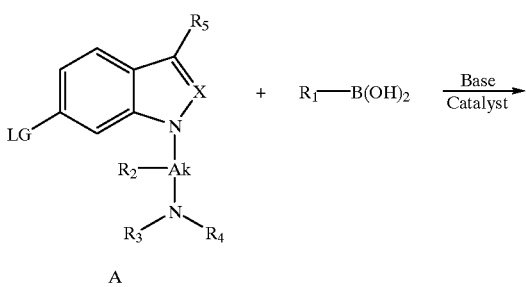

A

Alternatively, such compounds may be prepared according to Scheme 3, wherein intermediate A is converted to trialkyl tin derivative G upon treatment with a tin reagent such as hexamethylditin or hexabutyiditin in the presence of a catalyst such as tetrakis(triphenylphosphine) palladium (0). Treatment of intermediate G with, for example, a derivative of the desired $R_1$ group containing an appropriate group (LG) gives product H.

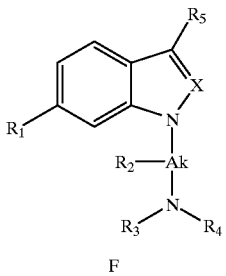

F

Scheme 3

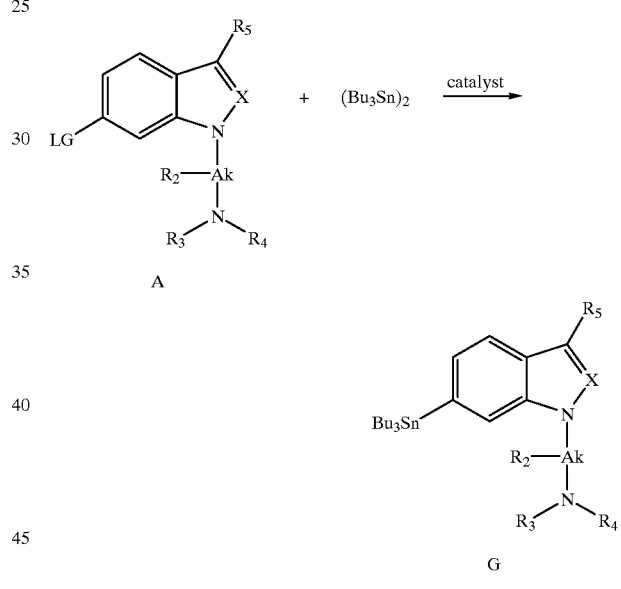

6-Heterocyclic substituents can be introduced as shown in scheme 3a, below, by the treatment of intermediate A with an organozinc intermediate in the presence of a nickel catalyst to give product F', or with a cyclic amine in the presence of a palladium catalyst to give product F".

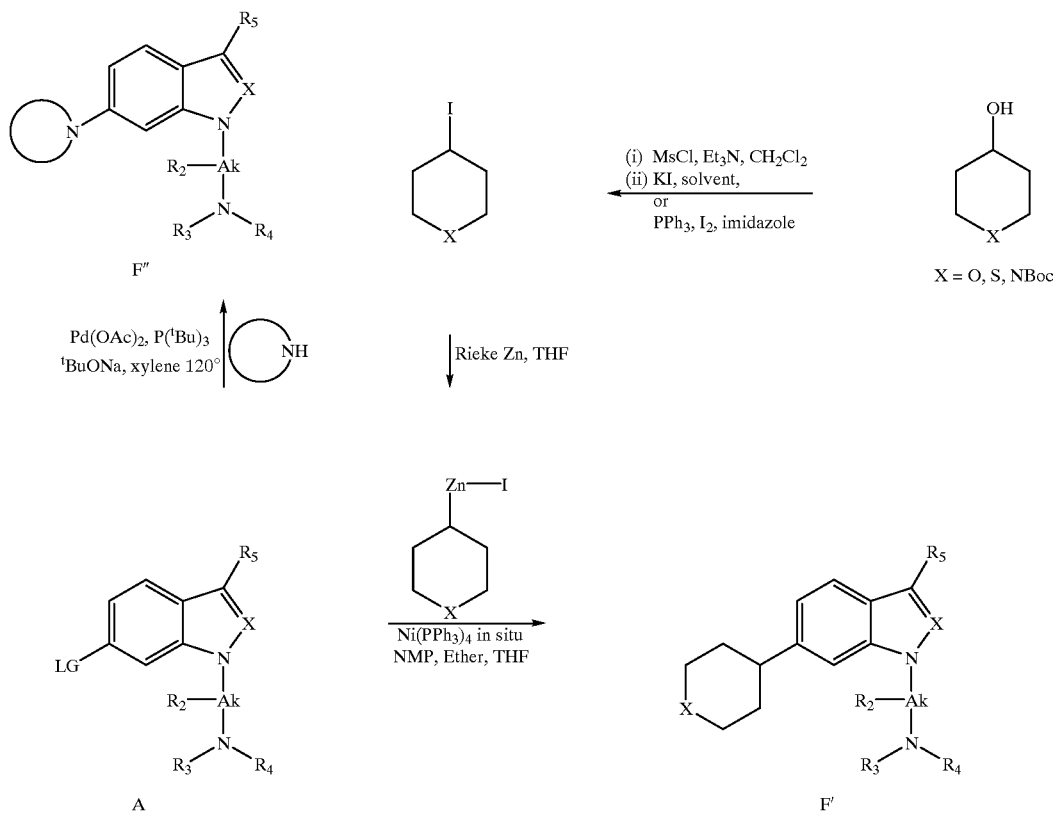

Substituents at the 3-position of the indole ring may be introduced as shown in Scheme 4.

3-substituents can also be introduced as shown in Scheme 5. Intermediate L can then be elaborated at the 1-position using standard chemistry, for example that shown in Schemes 7 and 8.

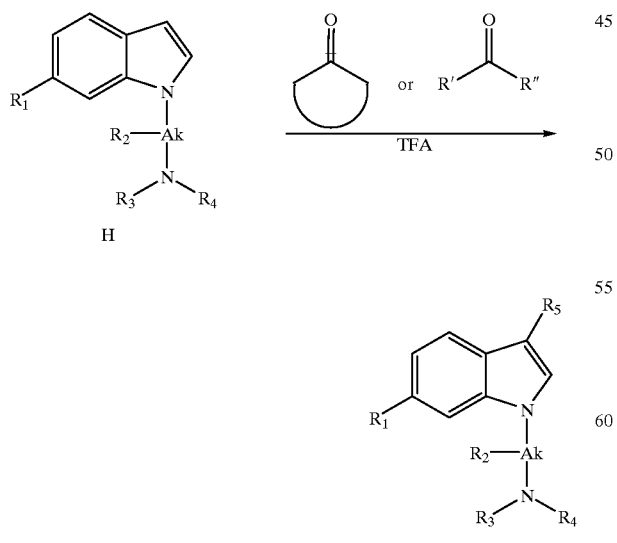

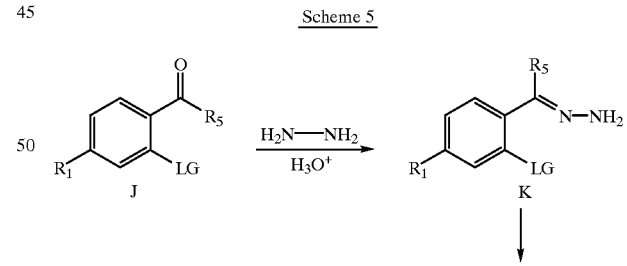

Alternatively, the 1-substituent can be introduced before formation of the indazole ring, as shown in scheme 6.

Scheme 6

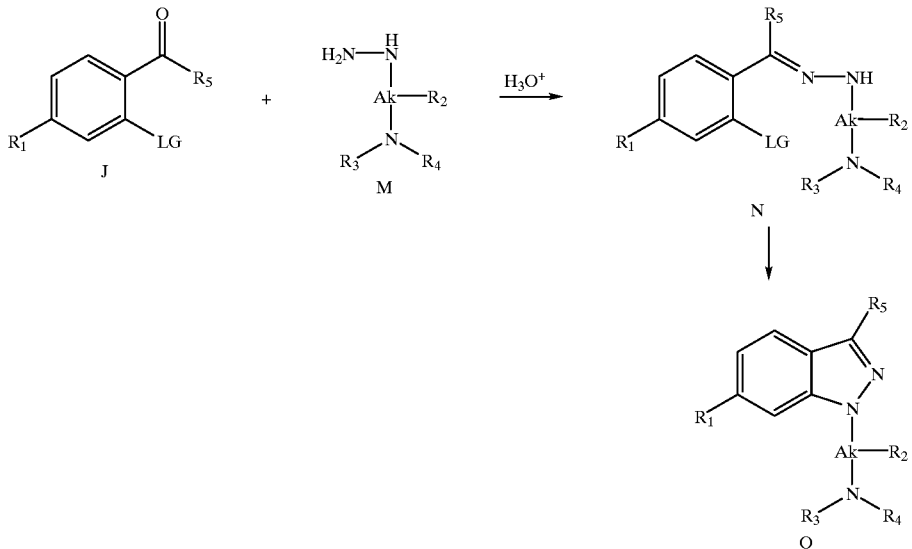

For compounds where X represents N and the 1-substituent is a 2-aminoethyl derivative, the route outlined in Scheme 7 was used.

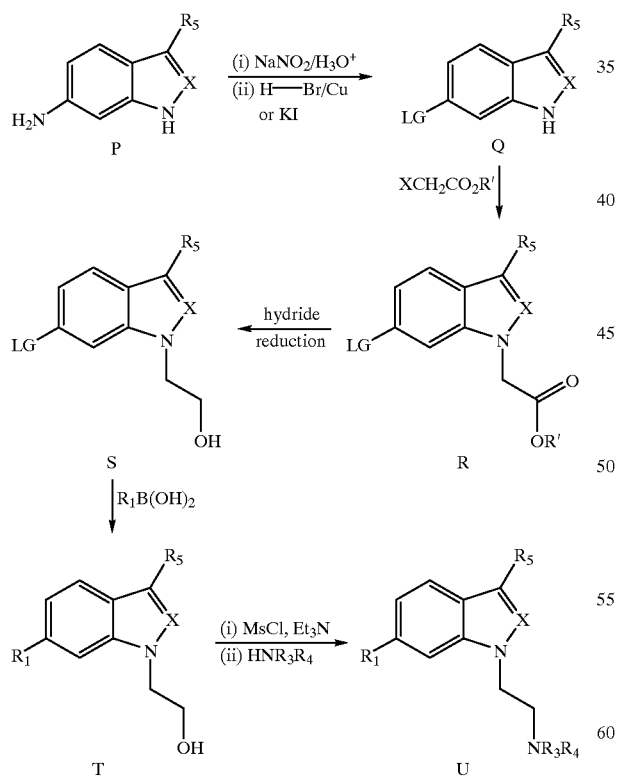

The substituent on the indole nitrogen can be introduced in a number of ways, some of which are outlined in Scheme 8. The 6-substituent can then be introduced as shown in the preceding schemes.

For example, a 2-aminoethyl substituent can be introduced by treatment of the 1-mesylate derived from indole V with an appropriate alkoxide. The 3-carbon homologue in both the indole and indazole series can be introduced by treatment of the 1-H compound X with 1-chloro-3-iodopropane, followed by treatment of the resulting chloro compound with an appropriate amine. Compounds in which $R_2$ is an alkyl group can be prepared, for example, by treatment of 1-H compound X with a substituted epoxide, followed by treatment of the resulting alcohol Z with an appropriate amine.

Compounds in which one of $R_3$ or $R_4$ and $R_2$ form a ring (compounds BB and CC in Scheme 8) can be prepared by treatment of the 1-H compound with an appropriate amino alcohol. Interestingly, the reaction with 2-Hydroxymethyl-N-methyl-piperidine gives rise to two products, one of which is a product of ring expansion.

Scheme 8

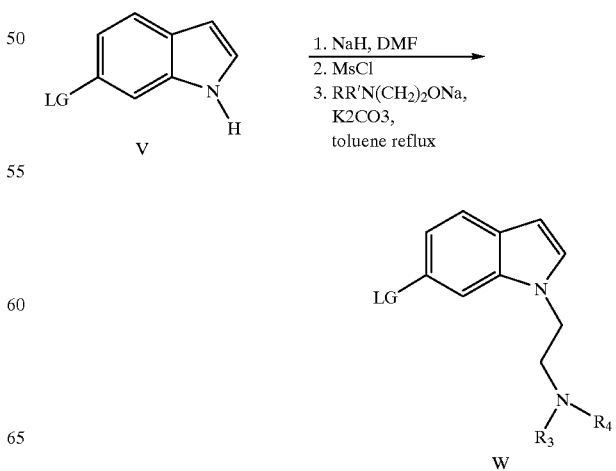

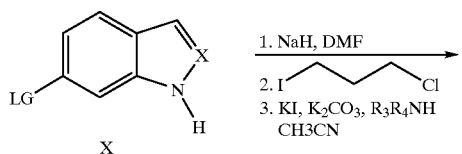

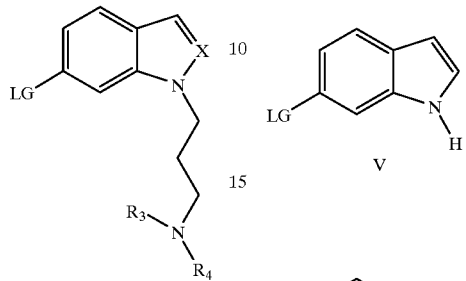

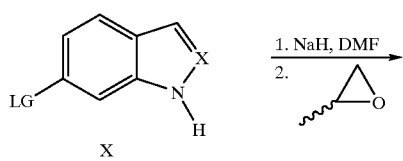

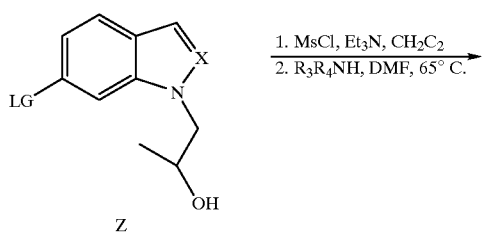

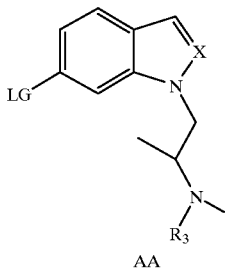

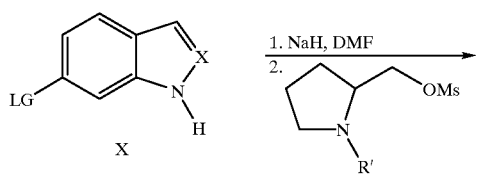

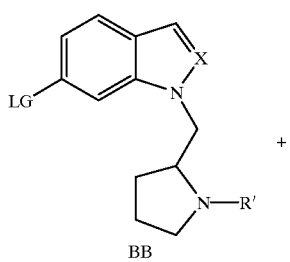

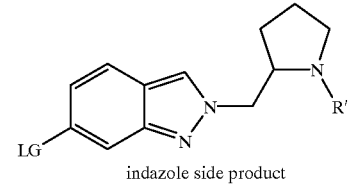

indazole side product

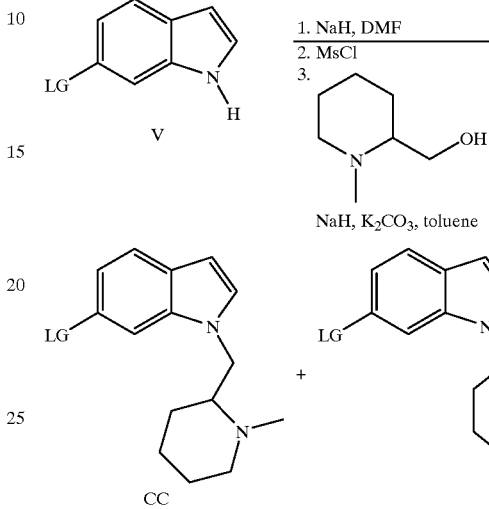

It should be appreciated that one skilled in the art would realize that the sequence of reactions described above can be varied. For example, in Scheme 4, above, the group at the indole 3-position may be incorporated into the molecule before the addition of the group at the indole 6-position.

In some cases, the chemistries outlined above may have to be modified, for instance by use of protecting groups, to prevent side reactions due to reactive groups, such as reactive groups attached as substituents. This may be achieved be means of conventional protecting groups, as described in *Protective Groups in Organic Chemistry*, ed. McOmie, J. F. W. Plenum Press, 1973; and Greene, T. W. & Wuts, P. G. M., *Protective Groups in Organic Synthesis*, John Wiley & Sons, 1991.

In another embodiment of the invention, the present compounds can be used to distinguish 5-HT$_{1D}$ receptors from other receptor subtypes, for example glutamate or opioid receptors, within a population of receptors, and in particular to distinguish between the 5-HT$_{1D}$ and other 5-HT receptor subtypes. The latter can be achieved by incubating preparations of the 5-HT$_{1D}$ receptor and one of the other 5-HT receptor subtypes (for example 5-HT$_{1B}$) with a 5-HT$_{1D}$-selective compound of the invention and then incubating the resulting preparation with a radiolabeled serotonin receptor ligand, for example [$^3$H]-serotonin. The 5-HT$_{1D}$ receptors are then distinguished by determining the difference in membrane-bound activity, with the 5-HT$_{1D}$ receptor exhibiting lesser radioactivity, i.e., lesser [$^3$H]-serotonin binding, than the other 5-HT receptor subtype.

In another aspect of the invention, a compound of the invention is provided in labeled form, such as radiolabeled form, e.g. labeled by incorporation within its structure $^3$H or $^{14}$C or by conjugation to $^{125}$I. In another aspect of the invention, the compounds in labeled form can be used as competitive ligands to identify 5-HT$_{1D}$ receptor ligands by techniques common in the art. This can be achieved by incubating the receptor or tissue in the presence of a ligand candidate and then incubating the resulting preparation with an equimolar amount of radiolabeled compound of the invention. 5-$HT_{1D}$ receptor ligands are thus revealed as those that are not significantly displaced by the radiolabeled compound of the present invention. Alternatively, 5-$HT_{1D}$ receptor ligand candidates may be identified by first incubating a radiolabeled form of a compound of the invention, then incubating the resulting preparation in the presence of the candidate ligand. A more potent 5-$HT_{1D}$ receptor ligand will, at equimolar concentration, displace the radiolabeled compound of the invention.

A radiolabeled compound of Formula I may be prepared using standard methods known in the art. For example, tritium may be incorporated into a compound of Formula I using standard techniques, for example by hydrogenation of a suitable precursor to a compound of Formula I using tritium gas and a catalyst. Alternatively, a compound of Formula I containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis (triphenylphosphine) palladium (0) in an inert solvent, such as dioxane, and at elevated temperatures, suitably 50–100° C.

The present compounds are useful as pharmaceuticals for the treatment of various conditions in which the use of a 5-$HT_{1D}$ ligand is indicated, such as for the treatment of migraine, cluster headache and portal tension, a condition characterized by increased portal vein blood flow and typically associated with cirrhosis of the liver.

For use in medicine, the compounds of the present invention can be administered in a standard pharmaceutical composition. The present invention therefore provides, in a further aspect, pharmaceutical compositions comprising a pharmaceutically acceptable carrier and at least one compound of Formula I, or a pharmaceutically acceptable salt, solvate or hydrate thereof, in an amount effective to stimulate the 5-$HT_{1D}$ receptor.

The compounds of the present invention may be administered by any convenient route, for example by oral, parenteral, buccal, sublingual, nasal, rectal or transdermal administration. Appropriate pharmaceutical compositions will be formulated accordingly.

Compounds of Formula I and their stereoisomers, solvates, hydrates or pharmaceutically acceptable salts for oral administration can be formulated as liquids, for example syrups, suspensions, solutions or emulsions, or as solid forms such as tablets, capsules and lozenges, or they may be presented as a dry product for constitution with water or other suitable vehicle before use. A liquid formulation will generally consist of a suspension or solution of the compound (or pharmaceutically acceptable salt thereof) in a suitable pharmaceutical liquid carrier such as ethanol, glycerine, polyethylene glycol, oils, or water with a suspending agent (e.g. sorbitol syrup, methyl cellulose or hydrogenated edible fats), preservative (e.g. methyl or propyl p-hydroxybenzoates or sorbic acid), flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule. Alternatively, a dispersion or suspension can be prepared using any suitable pharmaceutical carrier, for example aqueous gums, celluloses, silicates or oils, and the dispersion or suspension filled into a soft gelatin capsule.

Compounds of the present invention may be formulated for parenteral administration by injection, including using conventional catheterisation techniques or infusion. Formulations for injection may be presented in unit dosage form, e.g. in ampoules, or in multi-dose containers, with an added preservative. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil, and may contain formulatory agents such as suspending, stabilizing and/or dispersing agents. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form, in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer. Capsules and cartridges of, for example, gelatin for use in an inhaler or atomizing device may be formulated containing a powder mix of a compound of the invention and a suitable powder base such as lactose or starch.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are prepared in the form of, for example, suppositories or retention enemas, and may contain a conventional suppository base such as cocoa butter or other glycerides.

A proposed dose of the compounds of the invention for oral, buccal, sublingual or rectal administration to a human (of about 70 kg body weight) for the treatment of migraine is 0.1 mg to 500 mg, for example 0.5 mg to 100 mg, preferably 1 mg to 50 mg, of active ingredient per dose, administered up to 8 times per day, more usually 1 to 4 times per day. It will be appreciated that it may be necessary to make routine changes to the dosage depending on the age and weight of the patent as well as the severity of the condition to be treated. It should be understood that unless otherwise indicated, the dosages are referred to in terms of the weight of the compound of Formula I calculated as the free base.

The overall daily dosage administered by injection may be in the range of 0.1 mg to 100 mg, preferably between 0.1 mg and 50 mg, e.g., between 1 mg and 25 mg, of a compound of Formula I or a pharmaceutically acceptable salt, solvate or hydrate thereof calculated as the free base, the compound being administered 1 to 4 doses per day.

Aerosol formulations are preferably arranged so that each metered dose or "puff" delivered from a pressurized aerosol contains 0.1 to 10 mg of a compound of the invention, and each dose administered via capsules and cartridges in an inhaler contains 0.1 to 50 mg of a compound of the invention. Administration may be several times daily, for example 2 to 8 times, giving for example 1,2 or 3 doses each time. The overall daily dose by inhalation will be similar to that for oral administration.

The compounds of the invention may, if desired, be administered in combination with one or more other therapeutic agents, such as analgesics, anti-inflammatory agents and anti-nauseants.

EXPERIMENTAL EXAMPLES

Example 1

3-(1-Cyclohexenyl)-1-(2-(N,N-dimethylamino) ethyl)-6-(3-Pyridyl)-1H-indole (a) 1-(2-(N,N-Dimethylamino)ethyl)-6-(3-pyridyl)-1H-indole In a 25 mL round bottom flask equipped with a stir bar was added 6-Bromo-1-(2-(N,N-dimethylamino)ethyl)-1H-indole (0.10 g; 0.37 mmol), pyridine-3-boronic acid-1,3-propanediol cyclic ester (0.12 g; 0.74 mmol), toluene (10 mL), sodium carbonate (2M) (4 mL) and tetrakis (triphenylphosphine)palladium(0) (0.02 g; 0.04 mmol). The reaction mixture was refluxed overnight, filtered through a pad of celite and the solvent evaporated in vacuo. The residue was dissolved in ethyl acetate (30 mL) and successively washed with water (2×20 mL) and brine (20 mL). The organic phase was dried (sodium sulfate), filtered and the solvent was removed in vacuo. The crude residue was purified by column chromatography on silica gel using chloroform:ammonialmethanol (2N) (98:2) to yield the title compound as yellow oil (0.08 g; 85%). $^{13}$C NMR (CDCl$_3$): δ 148.6, 147.8, 137.9, 136.5, 134.5, 131.4, 129.3, 128.5, 123.5, 121.6, 118.9, 107.9, 101.3, 59.1, 45.8, 44.8.

(b) 3-(1-Cyclohexenyl)-1-(2-(N,N-dimethylamino-ethyl)-6-(3-pyridyl)-1H-indole

In a 20 mL vial equipped with a screw cap and a stir bar was added cyclohexanone (0.1 mL; 0.88 mmol), trifluoroacetic acid (1 mL) and acetic acid (0.75 mL). The mixture was heated at 110° C. under argon for 15 minutes. A solution of compound (a), above, (0.07 g; 0.25 mmol) in acetic acid (1 mL) was added. The resulting mixture was stirred for an additional 20 minutes at 110° C. The reaction mixture was quenched with potassium hydroxide (1N) (pH: 10; 80 mL) and extracted with ethyl acetate (30 mL). The organic phase was successively washed with water (3×30 mL), brine (30 mL), dried (sodium sulfate), filtered and solvent was removed in vacuo. The residue was purified by column chromatography on silica gel using chloroform:methanol (95:5) to yield the title compound (0.6 g; 64%). $^{13}$C NMR (CDCl$_3$): δ 148.6, 147.8, 138.0, 137.3, 134.5, 131.5, 130.9, 125.9, 123.5, 122.5, 121.8, 118.9, 118.4. 107.8, 45.8, 44.8, 34.2, 28.6, 25.8, 23.2, 22.5.

Example 2

3-(1-Cyclohexyl)-1-(2-(N,N-dimethylamino)ethyl)-6-(3-Pyridyl)-1H-indole

In a 10 mL round bottom flask equipped with a stir bar was added 10% Pd/C (~10 mg) and ethanol (3 mL). To this stirred suspension was added a solution of the compound of Example 1, above, (0.5 g; 0.13 mmol) in ethanol (2 mL), under argon. The mixture was purged with hydrogen gas in a balloon and stirred at room temperature for 14 h. The reaction mixture was filtered through a pad of celite and the solvent removed in vacuo. The crude residue was purified by column chromatography on silica gel using chloroform:ammonia/methanol (2N) (98:2) to yield the title compound as a yellow oil (0.02 g).

Example 3

1-(2-(N,N-Dimethylamino)ethyl)-6-(4-hydroxy-tetrahydro-thiopyran-4-yl)-1H-indole (i) 6-Bromo-1-(carboxyethyl)methyl-1H-indole To a 250 mL round bottom flask equipped with a stir bar was added 6-bromoindole (5 g; 25.5 mmol) and THF (50 mL). To this stirred solution, under argon, was added sodium bis(trimethylsilyl)amide (1M in tetrahydrofuran)(51 mL; 51 mmol). The resulting brown solution was stirred at room temperature for 1 h. At this point the mixture was cooled to −5° C., and a solution of ethyl bromoacetate (5.6 mL; 51 mmol) in THF (4 mL) added. The resulting brownish yellow precipitate was warmed to room temperature and further stirred for 1 h. The reaction mixture was diluted with ethyl acetate (100 mL) and the organic phase successively washed with water (3×50 mL) and brine (100 mL). The organic phase was separated, dried (sodium sulphate) and the solvent removed in vacuo to yield the title compound as a brown oil (crude weight: 7.3 g). $^{13}$C NMR (CDCl$_3$): δ 168.3, 137.4, 129.4, 123.2, 122.4, 115.6, 112.2,102.7, 61.7, 47.7, 14.2.

(ii) 6-Bromo-1-(2-hydroxyethyl)-1H-indole

To a 250 mL round bottom flask equipped with a stir bar was added compound (i), above, (3.0 g; 10.6 mmol) and THF (50 mL). The mixture was cooled to 0° C. and diisobutylaluminium hydride (1M in toluene)(42.5 mL; 42.5 mmol) added. The reaction mixture was stirred at room temperature for 2 h, cooled to 0° C. and the quenched with sodium sulfate decahydrate. The resulting thick gel was refluxed for 1 h, after which it was filtered through a pad of celite. Upon removing the solvent in vacuo a yellow oil was isolated, which was subjected to column chromatography on silica gel using hexanes:ethyl acetate (90:10) to yield the title compound as a bright greenish-yellow oil (1.8 g; 71%). $^{13}$C NMR (CDCl$_3$): δ 136.9, 129.1, 127.5, 122.8,122.3, 115.3, 122.5, 101.8, 61.7, and 48.7.

(iii) 6-Bromo-1-(2-(N,N-dimethylamino)ethyl)-1H-indole

To a 125 mL Erlenmeyer flask equipped with a stir bar and a screw cap was added compound (ii), above, (1.48 g; 6.17 mmol) and THF (15 mL). The solution was cooled to 0° C. and triethylamine (5.16 mL; 37 mmol) and methane sulfonyl chloride (0.53 mL; 6.79 mmol) added. The reaction mixture was stirred at 0° C. for 2 h. At this point dimethylamine (2M in tetrahydrofuran)(30.8 mL; 61.7 mmol) was added and the reaction mixture heated to 70° C. for 14 h. The reaction mixture was then cooled to room temperature, diluted with ethyl acetate (50 mL) and the organic phase successively washed with water (3×30 mL), brine (30 mL), dried (sodium sulfate), filtered and the solvent removed in vacuo. The crude residue was purified by column chromatography on silica gel using dichloromethane:ammonia/methanol (2N) (99:1) to yield the title compound as a brown oil (1.2 g; 73%). $^{13}$C NMR (CDCl$_3$): δ 136.8, 128.7, 127.4, 122.6, 122.2, 115.1, 122.3, 101.6, 58.9, 45.8, and 44.8.

(iv) 1-(2-(N N-dimethylamino)ethyl)-6-(4-hydroxy-tetrahydrothiopyran-4-yl)-1H-indole To a 25 mL flame-dried round bottom flask was added compound (iii), above, (0.24 g; 0.9 mmol) and THF (5 mL).

The mixture was cooled to −78° C. and n-BuLi (1.6M in hexanes)(1.41 mL; 2.25 mmol) added dropwise. The reaction mixture was stirred at −78° C. for 1 h. Tetrahydrothiopyran-4-one (0.52 g, 4.51 mmol) dissolved in tetrahydrofuran (5 mL) was then added and the resulting mixture warmed to −5° C. The mixture was stirred at this temperature for 1 h before being poured into ice cold pH 7 buffer (15 mL), followed by extraction with ethyl acetate (30 mL). The organic phase was successively washed with water (25 mL), brine (25 mL), dried (sodium sulfate), filtered and the solvent was removed in vacuo. The crude residue was subjected to column chromatography on silica gel using chloroform:ammonia/methanol (2N) (98:2) to yield the title compound as a white solid (0.20 g; 75%). $^{13}$C NMR (CDCl$_3$): δ 143.2, 135.9, 128.6, 127.5, 120.9, 116.3, 104.8, 101.0, 72.1, 59.1, 45.7, 44.5, 40.2, 24.5.

In a similar fashion, the following compounds were prepared:
(b) 1-(3-(N,N-dimethylamino)propyl)-6-(4-hydroxy-tetrahydrothiopyran-4-yl)-1H-indole: (229.2 mg, 67%); from 6-bromo-1-(3-(N,N-dimethylamino)propyl)indole (300.0 mg, 1.07 mmol), nBuLi (1.6M, 1.67 mL, 2.67 mmol) and tetrahydrothiopyran-4-one (371.8 mg, 3.20 mmol).
(c) 1-(2-(N,N-dimethylamino)ethyl)-6-(N-methyl-4-hydroxypiperidin4-yl)-1H-indole: (92.0 mg, 311%); from 6-bromo-1-(2-(N,N-dimethylamino)ethyl) indole (261.9 mg, 0.981 mmol), nBuLi (1.6M, 1.35 mL, 2.16 mmol) and N-methyl-4-piperidone (560.0 mg, 4.91 mmol).
(d) 1-(2-(pyrrolidinyl)ethyl-6-(4-hydroxy-tetrahydropyran-4-yl)-1H-indole: (69.0 mg, 14%); from 6-bromo-1-(2-pyrrolidinyl)ethyl indole (462.0 mg, 1.58 mmol), nBuLi (1.6M, 2.17 mL, 3.47 mmol) and tetrahydro-4H-pyran-4-one (0.73 mL, 7.88 mmol).
(e) 1-(2-(N,N-diethylamino)ethyl)-6-(4-hydroxy-tetrahydrothiopyran-4-yl)-1H-indole: (102.1 mg, 30%); from 6-bromo-1-(2-(N,N-diethylamino)ethyl) indole (300.0 mg, 1.01 mmol), nBuLi (2.5M, 1.01 mL, 2.53 mmol) and tetrahydrothiopyran-4-one (590.0 mg, 5.06 mmol).
(f) 1-(N-Cyclopropylamino)ethyl)-6-(4-hydroxy-tetrahydrothiopyran-4-yl)-1H-indole: (34.2 mg, 8%); from 6-bromo-1-(N-Cyclopropylamino)ethyl indole (400.0 mg, 1.32 mmol), nBuLi (2.5M, 1.32 mL, 3.30 mmol) and tetrahydrothiopyran-4-one (760.0 mg, 6.59 mmol).

Example 4

1-(2-(N,N-dimethylamino)ethyl)-6-(6H-2,3-dihydrothiopyran-4-yl)-1H-indole

To a 15 mL vial equipped with a screw cap and a stir bar was added the compound of example 2, above, (0.10 g; 0.33 mmol), THF (5 mL) and trifluoroacetic acid (8–10 drops). The reaction mixture was heated to 79° C. for 40 minutes before being diluted with ethyl acetate (10 mL), neutralized with sodium hydroxide (1N) (30 mL) and the organic phase separated, successively washed with water (2×25 mL) and brine (25 mL), dried (sodium sulfate), filtered and the solvent removed in vacuo. The crude residue was subjected to column chromatography on silica gel using chloroform:ammonialmethanol (2N) (98:2) to yield the title compound as yellow oil (0.05 g; 50%). $^{13}$C NMR (CDCl$_3$): δ 139.3, 137.0, 136.1, 128.5, 127.9, 120.8, 120.7, 117.8, 106.2, 101.2, 59.1, 45.8, 44.7, 29.3, 26.4, 25.7.

In a similar fashion, the following compounds were prepared:
(b) 1-(3-(N,N-dimethylamino)propyl)-6-(6H-2,3-dihydrothiopyran-4-yl)-1H-indole: (29.2 mg, 16%); from 6-(4-hydroxy-tetrahydrothiopyran-4-yl)-1-(3-(N,N-dimethylamino)propyl)indole (190.0 mg, 0.60 mmol) and TFA (10 drops) in THF (5 mL).
(c) 1-(2-(N,N-dimethylamino)ethyl)-6-(N-methyl-2,3-dihydropiperidin-4-yl)-1H-indole: (28.9 mg, 419%); from 1-(2-(N,N-dimethylamino)ethyl)-6-(N-methyl-4-hydroxypiperidin-4-yl) indole (75.0 mg, 0.249 mmol) and TFA (1 mL) in THF (5 mL).
(d) 1-(2-(pyrrolidinyl)ethyl-6-(2,3-dihydropyran-4-yl)-1H-indole: (25.0 mg, 66%); from 1-(2-(pyrrolidinyl)ethyl-6-(4-hydroxy-tetrahydropyran-4-yl) indole (40.0 mg, 0.127 mmol) and TFA (5 drops) in THF (5 mL).
(e) 1-(2-(N,N-diethylamino)ethyl)-6-(2,3-dihydrothiopyran-4-yl)-1H-indole: (6.3 mg, 6%); from 1-(2-(N,N-diethylamino)ethyl)-6-(4-hydroxy-tetrahydrothiopyran-4-yl)- indole (120.0 mg, 0.360 mmol) and TFA (10 drops) in THF (4 mL).
(f) 1-(N-Cyclopropylamino)ethyl-6-(2,3-dihydrothiopyran-4-yl)-1H-indole: (3.0 mg,12%); from 1-(N-Cyclopropylamino)ethyl-6-(4-hydroxy-tetrahydrothiopyran-4-yl) indole (25.0 mg,0.084 mmol) and TFA (10 drops) in THF (1 mL).

Example 5

1-(2-(N,N-dimethylamino)ethyl)-6-(tetrahydrothiopyran-4-yl))-1H-indole

To a 10 mL round bottom flask equipped with a stir bar was added 10% Pd/C (1 scoop) and ethanol (3 mL). To this stirred suspension was added a solution of the compound of example 3, above, (0.4 g; 0.12 mmol) in ethanol (3 mL) under argon. The mixture was purged with hydrogen gas in a balloon and stirred at room temperature for 14 h. The reaction mixture was filtered through a pad of celite and the solvent removed in vacuo. The crude residue was purified by column chromatography on silica gel using dichloromethane:ammonia/methanol (2N) (98:2) to yield the title compound as yellow oil (0.02 g; 48%). $^{13}$C NMR (CDCl$_3$): δ 140.8, 136.2, 127.9, 127.1, 120.9, 118.9, 106.8, 101.1, 59.0, 45.8, 44.8, 44.6, 35.8, 29.6.

In a similar fashion, the following compounds were prepared:
(b) 1-(3-(N,N-dimethylamino)propyl)-6-(tetrahydrothiopyran-4-yl)-1H-indole: (11.0 mg, 54%); from 1-(3-(N,N-dimethylamino)propyl)-6-(6H-2,3-dihydrothiopyran-4-yl)indole (20.0 mg, 0.07 mmol).
(c) 1-(2-(N,N-dimethylamino)ethyl)-6-(N-methyl-piperidin4-yl)-1H-indole: (8.3 mg, 36%); from 1-(2-(N,N-dimethylamino)ethyl)-6-(N-methyl-2,3-dihydropiperidin-4-yl) indole (22.7 mg, 0.080 mmol).
(d) 1-(2-(pyrrolidinyl)ethyl-6-(tetrahydropyran-4-yl)-1H-indole: (18.6 mg, 74%); from 1-(2-(pyrrolidinyl)ethyl-6-(2,3-dihydropyran-4-yl) indole (25.0 mg, 0.084 mmol).
(e) 1-(2-(N,N-diethylamino)ethyl)-6-(tetrahydropyran-4-yl)-1H-indole: (10.0 mg, 33%); from 1-(2-(N,N-diethylamino)ethyl)-6-(2,3-dihydropyran-4-yl) indole (30.0 mg, 0.095 mmol).

Example 6

6-(4-hydroxy-tetrahydropyran-4-yl)-1-(2-(N,N-dimethylamino)ethyl)-1H-indole (i) 6-Bromo-(1-Methanesulphonyl)-1H-indole To a solution of 6-Bromoindole (1.82 g, 9 mmol) in DMF at 0° C. was added NaH (446 mg, 18 mmol). The mixture was allowed to warm to room temperature and stirred for 15 min. The reaction was then cooled to 0° C., MeSO$_2$Cl (1.55 g, 13.5 mmol) added and the mixture stirred at this temperature for 1.5 h before being quenched with ice and diluted with ethyl acetate. The organic extract was washed with brine and dried over anhydrous Na$_2$SO$_4$. The crude residue was purified by flash chromatography to give the title product as a white solid (782 mg, 29% yield).

(ii) 6-Bromo-1-(2-(N,N-dimethylamino)ethyl)-1H-indole

To a powdered suspension of NaH (55 mg, 4.8 mmol) in toluene (4 mL) was added 2-(N,N-dimethylamino)ethanol (321 mg, 3.6 mmol). The mixture was stirred for 10 minutes, after which compound (i), above, (751 mg, 2.4 mmol) was added and the mixture refluxed 16 h. The mixture was allowed to cool to room temperature and then diluted with CH$_2$Cl$_2$. The organic extract was washed with water and brine and dried over anhydrous Na$_2$SO$_4$. The crude residue was purified by flash chromatography to give the title product as a white solid (390 mg, 61% yield).

(iii) 6-(4-hydroxy-tetrahydropyran-4-yl)-1-(2-(N,N-dimethylamino)ethyl)-1H-indole To a solution of compound (ii), above, (380 mg, 1.4 mmol) in THF (5 mL) at −78° C. was added n-BuLi (1 mL, 1.6 M sol. in hexane, 1.6 mmol). The mixture was stirred at −78° C. for 20 min. Tetrahydro-4H-pyran-4-one (280 mg, 2.8 mmol) dissolved in THF (1 mL) was added and the reaction mixture stirred at −78° C. for 2 hrs. The mixture was then quenched with NH$_4$Cl (saturated) and extracted with ethyl acetate. The organic extract was washed with brine and dried over anhydrous Na$_2$SO$_4$. The crude residue was purified by flash chromatography to give the title product as a yellow solid (150 mg, 37% yield).

In a similar fashion, the following compounds were prepared:
(b) 6-Bromo-1-(N-methylpiperidin-2-yl)methyl)-1H-indole (220 mg, 57.2%) and 6-bromo-1-(N-methyl-azepan-3-yl)-1H-indole (94 mg, 24.4%); from 6-bromo-1-methanesulfonyl-1H-indole (344 mg, 1.25 mmol) and N-methylpiperidine-2-methanol (395 mg, 2.5 mmol) with NaH (53 mg, 2.2 mmol) and potassium carbonate (325 mg, 2.35 mmol) in toluene (10 mL) at 100° C. overnight.

Example 7

6-(6H-2,3-dihydropyran-4-yl)-1-(2-(N,N-dimethylamino)ethyl)-1H-indole

To a solution of the compound of Example 6, above, (150 mg, 0.52 mmol) in THF (5 mL) was added trifluroacetic acid (1 mL). The mixture was refluxed for 1.5 h, diluted with NaOH and extracted with CH$_2$Cl$_2$. The organic extract was washed with brine and dried over anhydrous Na$_2$SO$_4$. The crude residue was purified by flash chromatography to give the title product as a white solid (94 mg, 67% yield)

Example 8

6-(tetrahydropyran-4-yl)-1-(2-(N,N-dimethylamino)ethyl)-1H-indole

A solution of the compound of Example 7, above, (12 mg, 0.04 mmol) in MeOH (0.5 mL) was added to a suspension of Pd/C in MeOH (1 mL) under argon. The mixture was purged with hydrogen gas in a balloon and stirred at room temperature for 12 h. The reaction mixture was filtered through celite and the solvent removed in vacuo. The crude residue was purified by flash chromatography to give the title product as a yellow oil (7 mg, 58%).

Example 9

6-Bromo-1-(2-(N,N-dimethylamino)ethyl)-1H-indazole (i) 6-Bromo-1H-indazole

Sodium nitrite (315 mg, 4.56 mmol) was added in 2 portions to an ice-cooled suspension of 6-aminoindazole (500 mg, 3.8 mmol) in water (0.4 mL) and hydrobromic acid (48%, 1.8 mL). The reaction mixture was stirred for 10 minutes longer than required for the brown gas to disappear. Copper powder (35 mg, 0.55 mmol) was then added and the mixture heated gently until nitrogen evolution began. The reaction mixture was then alternately heated and cooled to control the rate of reaction. When nitrogen evolution ceased, the reaction mixture was heated at 90° C. for 30 minutes, cooled to room temperature, neutralized with aqueous sodium hydroxide and the product extracted into ethyl acetate. The organic layer was washed sequentially with water and brine, dried over sodium sulfate and the solvent removed in vacuo. Flash chromatography on silica gel (20–40% ethyl acetate in hexane) yield the title product (119 mg, 16%).

(ii) Ethyl 2-(6-bromo-1H-indazol-1-yl)acetate

Sodium hydride (62 mg, 95%, 2.45 mmol) was added to an ice-cooled solution of the above compound (298.2 mg, 1.5 mmol) in DMF (3 mL). After stirring for 20 minutes at 0° C., ethyl 2-bromoacetate (0.30 mL, 2.7 mmol) was added and the mixture stirred at room temperature for 3 h. The reaction was quenched by partitioning between water and ethyl acetate. The organic layer was washed sequentially with water and brine, dried over sodium sulfate and the solvent removed in vacuo. Flash chromatography (silica gel, 15–20% ethyl acetate in hexane) yielded the title product (242 mg, 57%).

(iii) (6-Bromo-1H-indazol-1-yl)ethan-2-ol

DIBAL-H (5 mL, 1.5 M, 7.5 mmol) in toluene was added to a solution of the above compound (530 mg, 1.87 mmol) in tetrahydrofuran (10 mL) at 0° C. After stirring at 0° C. for 15 min the ice bath was removed and the reaction mixture stirred for 2 h at room temperature, quenched with sodium sulfate decahydrate and the product taken into ethyl acetate, filtered to remove the solid residue, and the solvent removed in vacuo. This yielded the title product as a white solid which was used without further purification (451 mg, 96%).

(iv) 6-Bromo-1-(2-(N N-dimethylamino)ethyl)-1H-indazole

Methanesulfonyl chloride (0.20 mL, 2.6 mmol) was added to an ice-cooled solution of the above compound (550.6 mg, 2.28 mmol) and triethylamine (0.65 mL, 4.7 mmol) in dichloromethane (10 mL). After stirring at 0° C. for 45 min, the reaction was quenched by dilution with dichloromethane and washed sequentially with sodium hydrogen sulfate (aqueous, 1M), sodium bicarbonate (aqueous, saturated) and brine. The organic layer was dried over sodium sulfate and the solvent was removed in vacuo. A solution of dimethylamine (12 mL, 2 M, 24 mmol) in tetrahydrofuran was added to the above crude product and the resulting mixture gently refluxed for 36 h. After cooling to room temperature, the reaction mixture was partitioned between water and ethyl acetate. The organic layer was washed sequentially with water and brine, dried over sodium sulfate and the solvent was removed in vacuo. Flash chromatography (silica gel, 2–4% 2M methanolic ammonia in dichloromethane) yielded the title product (525 mg, 86%).

In a like manner (that is, via the methanesulfonates derived from the alcohols listed below), the following compounds were prepared:
(b) 1-(2-(N,N-diethylamino)ethyl)-6-(3-thienyl)-1H-indazole: (20 mg, 80%); from 2-(6-(3-thienyl)-1H-indazol-1-yl)ethan-2-ol (0.083 mmol) and diethylamine (0.10 mL, 0.97 mmol).
(c) 1-(2-(N,N-dipropylamino)ethyl)-6-(3-thienyl)-1H-indazole: 25.3 mg, 93%); from 2-(6-(3-thienyl)-1H-indazol-1-yl)ethan-2-ol (0.083 mmol) and dipropylamine (0.13 mL, 0.95 mmol).
(d) 1-(2-(N-methylamino)ethyl)-6-(3-thienyl)-1H-indazole: (17.5 mg, 82%); from 2-(6-(3-thienyl)-1H-indazol-1-yl)

ethan-2-ol (0.083 mmol) and methylamine (0.50 mL, 2M in THF, 1 mmol).

(e) 1-(2-(N-allylamino)ethyl)-6-(3-thienyl)-1H-indazole: (18.6 mg, 79%); from 2-(6-(3-thienyl)-1H-indazol-1-yl)ethan-2-ol (0.083 mmol) and allylamine (0.08 mL, 1.07 mmol).

(f) 1-(2-(N-benzylamino)ethyl)-6-(3-thienyl)-1H-indazole: (26.0 mg, 94%); from 2-(6-(3-thienyl)-1H-indazol-1-yl)ethan-2-ol (0.083 mmol) and benzylamine (0.09 mL, 0.8 mmol).

(g) 1-(2-(N-isopropylamino)ethyl)-6-(3-thienyl)-1H-indazole: from 2-(6-(3-thienyl)-1H-indazol-1-yl)ethan-2-ol (0.083 mmol) and isopropylamine (0.08 mL, 0.94 mmol).

(h) 1-(2-(N-(1-benzylpyrrolidin-3-yl)amino)ethyl)-6-(3-thienyl)-1H-indazole: (32.0 mg, 95%); from 2-(6-(3-thienyl)-1H-indazol-1-yl)ethan-2-ol (0.083 mmol) and (1-benzylpyrrolidin-3-yl)amine (or 1-benzyl-3-aminopyrrolidine) (160 mg, 0.91 mmol).

(i) 1-(2-(N-pyrrolidinyl)ethyl)-6-(3-thienyl)-1H-indazole: (21.5 mg, 87%); from 2-(6-(3-thienyl)-1H-indazol-1-yl)ethan-2-ol (0.083 mmol) and pyrrolidine (0.08 mL, 0.96 mmol).

(j) 1-(2-(N-pyrrolin-3-yl)ethyl)-6-(3-thienyl)-1H-indazole: (14.2 mg, 58%); from 2-(6-(3-thienyl)-1H-indazol-1-yl)ethan-2-ol (0.083 mmol) and 3-pyrroline (0.08 mL, 1.04 mmol).

(k) 1-(2-(N-piperidinyl)ethyl)-6-(3-thienyl)-1H-indazole: (19.3 mg, 74%); from 2-6-(3-thienyl)-1H-indazol-1-yl)ethan-2-ol (0.083 mmol) and piperidine (0.10 mL, 1.01 mmol).

(l) 1-(2-(N-(3tert-butoxycarbonylamino)pyrrolidinyl)ethyl)-6-(3thienyl)-1H-indazole: (19.2 mg, 56%); from 2-(6-(3-thienyl)-1H-indazol-1-yl)ethan-2-ol (0.083 mmol) and 3-tert-butoxycarbonylamino)pyrrolidine (77.8 mg, 0.42 mmol).

(m) 6-Bromo-1-(2-(N,3-hydroxypyrrolidinyl)ethyl)-1H-indazole: (17.5 mg, 45%); from 2-(6-bromo-1H-indazol-1-yl)ethan-2-ol (0.126 mmol) and pyrrolidin-3-ol (0.04 mL, 0.48 mmol).

(n) (S)-6-Bromo-1-(2-(N-(2-hydroxymethyl)pyrrolidinyl)ethyl)-1H-indazole: (38.1 mg, 93%); from 2-(6-bromo-1H-indazol-1-yl)ethan-2-ol (0.126 mmol) and (S)-pyrrolidine-2-methanol (0.04 mL, 0.4 mmol).

(o) (R)-6-Bromo-1-(2-(N-(2-hydroxymethyl)pyrrolidinyl)ethyl)-1H-indazole: (37.6 mg, 92%); from 2-(6-bromo-1H-indazol-1-yl)ethan-2-ol (0.126 mmol) and (R)-pyrrolidine-2-methanol (0.04 mL, 0.4 mmol).

(p) 1-(2-(N-cyclopropylamino)ethyl)-64(3-thienyl)-1H-indazole: (31.1 mg, 87%); from 2-(6-(3-thienyl)-1H-indazol-1-yl)ethan-2-ol (31.4 mg, 0.127 mmol) and cyclopropylamine (0.25 mL, 3.6 mmol).

(q) 1-(2-(azetidin-1-yl)ethyl)-6-(3-thienyl)-1H-indazole: (34.1 mg, 91%); from 2-(6-(3-thienyl)-1H-indazol-1-yl)ethan-2-ol (31.4 mg, 0.127 mmol) and azetidine (250 mg, 4.4 mmol).

(r) 1-(2-(N-cyclopropylmethylamino)ethyl)-6-(3-thienyl)-1H-indazole: (18.6 mg, 52%); from 2-(6-(3-thienyl)-1H-indazol-1-yl)ethan-2-ol (31.4 mg, 0.127 mmol) and cyclopropylmethylamine (0.25 mL, 2.9 mmol).

Example 10

1-(2-(N,N-dimethylamino)ethyl)-6-(2-thienyl)-1H-indazole

A solution of 6-bromo-1-(2-(N,N-dimethylamino)ethyl)-1H-indazole (34 mg, 0.127 mmol), 2-thiopheneboronic acid (17.2 mg, 0.13 mmol), tetrakistriphenylphosphine palladium(0) (11 mg, 0.01 mmol) and sodium carbonate (aqueous, 1M, 0.33 mL) in toluene (0.5 mL) and ethanol (0.5 mL) was heated at reflux under an inert atmosphere for 14 h. After cooling to room temperature, the reaction was partitioned between ethyl acetate (75 mL) and brine (20 mL), the organic layer dried over sodium sulfate and the solvent removed in vacuo. Preparative thin layer chromatography (TLC) by elution with 3% triethylamine in ethyl acetate yielded the product (8.2 mg, 24%).

In a like manner, the following additional compounds were prepared:

(b) 1-(2-(N,N-dimethylamino)ethyl)-6-(3-thienyl)-1H-indazole: (34.4 mg, 100%); from 6-bromo-1-(2-(N,N-dimethylamino)ethyl)-1H-indazole (34 mg, 0.127 mmol) and 3-thiopheneboronic acid (19 mg, 0.15 mmol).

(c) 1-(2-(N,N-dimethylamino)ethyl)-6-(3-pyridinyl)-1H-indazole: (30.6 mg, 91%); from 6-bromo-1-(2-(N,N-dimethylamino)ethyl)-1H-indazole (34 mg, 0.127 mmol) and pyridine-3-boronic acid 1,3-propanediol cyclic ester (22 mg, 0.13 mmol).

(d) 1-(Ethan-2-ol)-6-(3-thienyl)-1H-indazole: (245 mg, 97%); from 6-bromo-1-(ethan-2-ol)-1H-indazole (248.7 mg, 1.03 mmol) and 3-thiopheneboronic acid (157 mg, 1.22 mmol).

(e) 1-(2-(N,3-hydroxypyrrolidinyl)ethyl)-6-(3-thienyl)-1H-indazole: (10.0 mg, 61%); from 6-bromo-1-(N,3-hydroxypyrrolidinyl)ethyl)-1H-indazole (16 mg, 0.052 mmol) and 3-thiopheneboronic acid (25 mg, 0.20 mmol).

(f) (S)-1-(2-(N-(2-hydroxymethyl)pyrrolidinyl)ethyl)-6-(3-thienyl)-1H-indazole: (17.5 mg, 51%); from (S)-6-bromo-1-(2-(N-(2-hydroxymethyl)pyrrolidinyl)ethyl)-1H-indazole (34.0 mg, 0.105 mmol) and 3-thiopheneboronic acid (25 mg, 0.20 mmol).

(g) (R)-1-(2-(N-(2-hydroxymethyl)pyrrolidinyl)ethyl)-6-(3-thienyl)-1H-indazole: (17.7 mg, 51%); from (R)-6-bromo-1-(2-(N-(2-hydroxymethyl)pyrrolidinyl)ethyl)-1H-indazole (34.0 mg, 0.105 mmol) and 3-thiopheneboronic acid (25 mg, 0.20 mmol).

(h) 1-(2-(N,N-diethylamino)ethyl)-6-(3-pyridinyl)-1H-indazole: (28 mg, 90% pure; 100%); from 6-bromo-1-(2-(N,N-diethylamino)ethyl)-1H-indazole (24.6 mg, 0.083 mmol) and pyridine-3-boronic acid 1,3-propanediol cyclic ester (23.9 mg, 0.147 mmol).

(i) 1-(2-(N,N-diethylamino)ethyl)-6-(furan-3-yl)-1H-indazole: (16.1 mg, 68%); from 6-bromo-1-(2-(N,N-diethylamino)ethyl)-1H-indazole (24.6 mg, 0.083 mmol) and furan-3-boronic acid (16.1 mg, 0.144 mmol).

(j) 1-(2-(N,N-diethylamino)ethyl)-6-(5-methyl-2-thienyl)-1H-indazole: (11.5 mg, 43%); from 6-bromo-1-(2-(N,N-diethylamino)ethyl)-1H-indazole (25.5 mg, 0.086 mmol) and 5-methylthiophene-2-boronic acid (22.1 mg, 0.155 mmol).

(k) 1-(2-(N,N-diethylamino)ethyl)-6-(4-methyl-2-thienyl)-1H-indazole: (24.1 mg, 90%); from 6-bromo-1-(2-(N,N-diethylamino)ethyl)-1H-indazole (25.4 mg, 0.086 mmol) and 4-methylthiophene-2-boronic acid (22.1 mg, 0.155 mmol).

(l) 1-(2-(N,N-diethylamino)ethyl)-6-(5-chloro2-thienyl)-1H-indazole: (11.3 mg, 39%); from 6-bromo-1-(2-(N,N-diethylamino)ethyl-1H-indazole (25.4 mg, 0.086 mmol) and 5-chlorothiophene-2-boronic acid (24.5 mg, 0.151 mmol).

(m) 1-(2-(N,N-diethylamino)ethyl)-6-(1-Boc-2-pyrrole)-1H-indazole: (24.4 mg, 76%); from 6-bromo-1-(2-(N,N-diethylamino)ethyl)-1H-indazole (24.9 mg, 0.084 mmol) and 1-Boc-pyrrole-2-boronic acid (31.0 mg, 0.147 mmol).

(n) 1-(2-(N,N-diethylamino)ethyl)-6-(benzo[b]2-thienyl)-1H-indazole: (27.1 mg, 93%); from 6-bromo-1-(2-(N,N-diethylamino)ethyl)-1H-indazole (24.6 mg, 0.083 mmol) and benzo[b]thiophene-2-boronic acid (25.6 mg, 0.144 mmol).

(o) 1-(2-(N,N-diethylamino)ethyl)-6-(benzofuran-2-yl)-1H-indazole: (26.8 mg, 96%); from 6-bromo-1-(2-(N,N-diethylamino)ethyl)-1H-indazole (24.8 mg, 0.084 mmol) and benzofuran-2-boronic acid (25.3 mg, 0.156 mmol).

(p) (R,S)-1-(2-(N,N-dimethylamino)propyl)-6-(3-pyridinyl)-1H-indole: (7.0 mg, 20%); from (R,S)-6-bromo-1-(2-(N,N-dimethylamino)propyl)-1H-indole (35.9 mg, 0.127 mmol) and pyridine-3-boronic acid 1,3-propanediol cyclic ester (24.6 mg, 0.15 mmol).

(q) (R,S)-1-(2-(N,N-dimethylamino)propyl)-6-(3-thienyl)-1H-indole: (16.8 mg, 46%); from (R,S)-6-bromo-1-(2-(N,N-dimethylamino)propyl)-1H-indole (35.7 mg, 0.127 mmol) and thiophene-3-boronic acid (21.5 mg, 0.17 mmol).

(r) 1-(N-methylpiperidin-2-yl)methyl)-6-3-thienyl-1H-indole: (8.4 mg, 57.6%); from 6-Bromo-1-(N-methylpiperidin-2-yl)methyl)-1H-indole indole (15 mg, 0.05 mmol) and 3-thipheneboronic acid (15 mg, 0.117 mmol).

(s) 1-(N-methyl-azepan-3-yl)-6-3-thienyl-1H-indole: (6.8 mg, 46.6%); from 6-bromo-1-(N-methyl-azepan-3-yl)-1H-indole (15 mg, 0.05 mmol) and 3-thiopheneboronic acid (15 mg, 0.117 mmol).

(t) 1-(2-(N,N-dimethylamino)ethyl)-6-(2-thienyl)-1H-indole: (23.5 mg); from 6-bromo-1-(2-(N,N-dimethylamino)ethyl)indole (50.0 mg, 0.19 mmol) and thiophene-2-boronic acid (47.9 mg, 0.37 mmol).

(u) 1-(2-(N,N-dimethylamino)ethyl)-64benzo[b]thiophene-2-yl)-1H-indole: (57.1 mg); from 6-bromo-1-(2-(N,N-dimethylamino)ethyl)indole (100.0 mg, 0.37 mmol) and benzo[b]thiophene-2-boronic acid (133.3 mg, 0.74 mmol).

(v) (S)-1-((N-methylpyrrolidin-2-yl)methyl)-6-(2-thienyl)-1H-indole: (8.7 mg); from (S)-6-bromo-1-((N-methylpyrrolidin-2-yl)methyl)indole (42.5 mg, 0.14 mmol) and thiophene-2-boronic acid (37.0 mg, 0.29 mmol).

(w) 1-(2-(N,N-dimethylamino)ethyl)-6-(3-pyridinyl)-1H-indole: (83.6 mg, 85%); from 6-bromo-1-(2-(N,N-dimethylamino)ethyl)indole (100.0 mg, 0.37 mmol) and pyridine-3-boronic acid-1,3-propanediol cyclic ester (120.6 mg, 0.74 mmol).

(x) (S)-1-((N-methylpyrrolidin-2-yl)methyl)-6-(pyridi-3-yl)-1H-indole: (30.6 mg, 62%); from (S)-6-bromo-1-((N-methylpyrrolidin-2-yl)methyl)indole (50.0 mg, 0.17 mmol) and pyridine-3-boronic acid-1,3-propanediol cyclic ester (55.6 mg, 0.34 mmol).

(y) 1-(2-(N,N-dimethylamino)ethyl)-6-(3thienyl)-1H-indole: (23.5 mg, 46%); from 6-bromo-1-(2-(N,N-dimethylamino)ethyl)indole (50.0 mg, 0.19 mmol) and thiophene-3-boronic acid (47.9 mg, 0.37 mmol).

(z) (R)-1-((N-methylpyrrolidin-2-yl)methyl)-6-(3-pyridinyl)-1H-indole: (37.0 mg, 75%); from (S)-6-bromo-1-((N-methylpyrrolidin-2-yl)methyl)indole (50.0 mg, 0.17 mmol) and pyridine-3-boronic acid-1,3-propanediol cyclic ester (55.6 mg, 0.34 mmol).

(aa) (R)-1-((N-methyl pyrrolidin-2-yl)methyl)-6-(3-thienyl)-1H-indole: (39.9 mg, 79%); from (S)-6-bromo-1-((N-methylpyrrolidin-2-yl)methyl)indole (50.0 mg, 0.17 mmol) and thiophene-2-boronic acid (43.6 mg, 0.34 mmol).

(bb) 1-(3-(N,N-dimethylamino)propyl)-6-(3-pyridinyl)-1H-indole: (9.8 mg, 13%); from 6-bromo-1-(3-(N,N-dimethylamino)propyl) indole (75.0 mg, 0.267 mmol) and pyridine-3-boronic acid 1,3-propanediol cyclic ester (87.0 mg, 0.534 mmol).

(cc) 1-(2-pyrrolidinyl)ethyl-6-(3-pyridinyl)-1H-indole: (9.3 mg, 49%); from 6-Bromo-1-(2-pyrrolidinyl)ethyl indole (19.0 mg, 0.065 mmol) and pyridine-3-boronic acid 1,3-propanediol cyclic ester (21.0 mg, 0.130 mmol).

(dd) 1-(2-(N,N-diethylamino)ethyl)-6-(3-pyridinyl)-1H-indole: (16.6 mg , 56%); from 6-bromo-1-(2-(N,N-diethylamino)ethyl) indole (30.7 mg, 0.101 mmol) and pyridine-3-boronic acid 1,3-propanediol cyclic ester (33.0 mg,0.202 mmol).

(ee) 1-(2-(N,N-diethylamino)ethyl)-6-(3-thiophene)-1H-indole: (65.1 mg, 100%); from 6-bromo-1-(2-(N,N-diethylamino)ethyl) indole (31.8 mg, 0.101 mmol) and 3-thiophene boronic acid (25.9 mg, 0.202 mmol).

(ff) 6-(3-thienyl)-1H-indazole: (237 mg, 71%); from 6-iodo-1H-indazole (403.5 mg, 1.65 mmol) and 3-thiopheneboronic acid (236.5 mg, 1.8 mmol).

Example 11

1-(2-(N,N-dimethylamino)ethyl)-6-tributylstannyl-1H-indazole

Argon was bubbled through a solution of 6-bromo-1-(2-(N,N-dimethylamino)ethyl)-1H-indazole (198 mg, 0.74 mmol) in toluene (4 mL) for 10 min prior to the addition of bis(tributylstannane) (0.88 mL, 1.74 mmol) and tetrakistriphenylphosphine palladium(0) (10–20 mg, catalytic). The resulting mixture was heated at reflux under an inert atmosphere for 18 h. After cooling to room temperature the solvent was removed in vacuo and the reaction mixture diluted with dichloromethane. Flash chromatography (silica gel, 1.5–4% 2M methanolic ammonia in dichloromethane) yielded the title product (315 mg, 89%).

Example 12

1(2-(N,N-dimethylamino)ethyl)-6-(4-pyridinyl)-1H-indazole

A solution of 1-(2-(N,N-dimethylamino)ethyl)-6-tributylstannyl-1H-indazole (49.1 mg, 0.10 mmol), 4-bromopyridine hydrochloride (21.6 mg, 0.11 mmol), tetrakistriphenylphosphine palladium(0) (10–20 mg, catalytic) in toluene (0.5 mL) was heated at reflux under an inert atmosphere for 18 h. After cooling to room temperature the reaction was quenched by the addition of aqueous sodium hydroxide (1 M, 2 mL) and water (10 mL), and the product extracted into ethyl acetate (50 mL). The organic layer was washed sequentially with water and brine, dried over sodium sulfate and the solvent removed in vacuo. Filtration through an SPE cartridge (Supelco, 6 mL, silica gel, 1000 mg, gradient from 0–10% 2M methanolic ammonia in dichloromethane) gave a crude product which was further purified by flash chromatography (silica gel, 4–10% 2M methanolic ammonia in dichloromethane) to give the title product (6.1 mg, 11%).

In a like manner, the following compound was prepared:

(b) 1-(2-(N,N-dimethylamino)ethyl)-6-(pyridin-2-yl)-1H-indole: (14.7 mg); from 6-bromo-1-(2-(N,N-dimethylamino)ethyl)-1H-indole (50.0 mg, 0.19 mmol), 2-tributylstannylpyridine (103.3 mg, 0.28 mmol) and tetrakis(triphenylphosphine) palladium(0) (21.6 mg,0.02 mmol) in toluene (5 mL).

(c) 1-(3-N,N-dimethylamino)propyl-6-(2-thiophene)-1H-indole: (27.6 mg, 43%) 6-Bromo-1-(3-N,N- dimethylamino)propyl-1H-indole (203.0 mg, 0.722 mmol) was dissolved in toluene (15 mL) and 2-tributylstanylthiophene (0.34 mL, 1.08 mmol) was added followed by tetrakistriphenylphosphine palladium (0) (20.0 mg). The reaction was allowed to reflux under Argon overnight. The reaction was then cooled, filtered through Celite and concentrated. The crude product was purified by column chromatography (2.5% 2M NH$_3$—MeOH in CH$_2$Cl$_2$) to yield the title compound.

Example 13

1-(2-(N,N-dimethylamino)ethyl)-6-(1-methyl-1,2,5,6-tetrahydro-4-pyridine)-1H-indazole (i) 1-Methyl-4-piperidone tosyl hydrazone 1-Methyl-4-piperidone (1.23 mL, 10 mmol) was added to a suspension of tosyl hydrazide (2.0 g, 10 mmol) in ethanol (4.0 mL). After several minutes at room temperature the solid dissolved to form a yellow solution. This solution was heated at reflux for 2.5 h, and cooled overnight in the freezer to crystallize. The solid product was obtained by filtration and rinsing with several portions of ethanol. (1.60 g, 57%)

(ii) 1-(2-(N,N-dimethylamino)ethyl)-6-(1-methyl-1,2,5,6-tetrahydro-4-pyridine)-1H-indazole TMEDA (0.4 mL) was added to a cooled (−78° C.) suspension of the above compound (116.7 mg, 0.41 mmol) in hexane (0.40 mL), and nBuLi (0.50 mL, 2.5 M, 1.25 mmol) added to give an orange-yellow mixture. After 10 min at −78° C., the reaction mixture was warmed to 0° C. for 20 min, to allow complete evolution of nitrogen gas. The mixture was cooled to −78° C. prior to the addition of triisopropyl borate (0.20 mL, 0.87 mmol), and then warmed to 0° C. After 1.5 h, the solvent was removed in vacuo, and 6-bromo-1-(2-(N,N-dimethylamino)ethyl)-1H-indazole (55.1 mg, 0.205 mmol), palladium (II) acetate (6.3 mg, 0.028 mmol) and triphenylphosphine (19 mg, 0.072 mmol) added. Toluene (1.0 mL), ethanol (1.0 mL) and sodium carbonate (2M, 0.8 mL, 1.6 mmol) were added under an inert atmosphere, and the reaction mixture gently refluxed for 20 h. After cooling to room temperature, the solvent was removed in vacuo, water (0.8 mL) was added, and the mixture passed through an EXTUBE (VARIAN, 3 mL tube, diatomaceous earth) and extracted into dichloromethane (15 mL). After evaporation of the solvent, flash chromatography (silica gel, 3–7% 2M methanolic ammonia in dichloromethane) yielded the title product (31.7 mg, 54%).

In a similar fashion, the following compound was prepared:

(b) (R,S)-1-(2-(N,N-dimethylamino)propyl)-6-(1-methyl-1,2,5,6-tetrahydro-4-pyridine)-1H-indole: (7.7 mg, 18%); from (R,S)-6-bromo-1-(2-(N,N-dimethylamino)propyl)-1H-indole (40.1 mg, 0.14 mmol) and 1-methyl-4-piperidone tosyl hydrazone (57 mg, 0.20 mmol).

Example 14

1-(2-(N-propylamino)ethyl)-6-(3-thienyl)-1H-indazole

A small scoop of palladium on carbon (10%~10 mg, catalytic) was added to a solution of 1-(2-(N-allylamino)ethyl)-6-(3-thienyl)-1H-indazole (15 mg, 0.053 mmol) in ethyl acetate (1 mL). The resulting mixture was stirred under an atmosphere of hydrogen gas in a balloon for 1 h. Filtration through an SPE cartridge (Supelco, 6 mL, silica gel, 1000 mg, gradient from 0–10% 2M methanolic ammonia in ethyl acetate) gave the title product (12.2 mg, 81%).

Example 15

1-(2-(N,N-dimethylamino)ethyl)-6-(N-methylpiperidin-4-yl)-1H-indazole

A small scoop of palladium on carbon (10%, approx. 10 mg, catalytic) was added to a solution of 1-(2-(N,N-dimethylamino)ethyl)-6-(1-methyl-1,2,5,6-tetrahydro-4-pyridine)-1H-indazole (28 mg, 0.1 mmol) in methanol (2.5 mL). The resulting mixture was stirred under an atmosphere of hydrogen gas in a balloon for 36 h.

The catalyst was removed by filtration through a pad of celite using 50% ethyl acetate in methanol (50 mL) to wash the solid. The solvent was removed in vacuo and flash chromatography (silica gel, 3–15% 2M methanolic ammonia in 10 dichloromethane) yielded 1-(2-(N,N-dimethylamino)ethyl)-6-(N-methylpiperidin-4-yl)-1H-indazole (11.2 mg, 40%).

Example 16

1-(2-(N,N-diethylamino)ethyl)-6-(tetrahydropyran-4-yl)-1H-indazole

Rieke zinc (5 g/100 mL, 1.25 mL, 0.96 mmol) was added to a flame-dried vial containing 4-iodotetrahydropyran (136.7 mg, 0.64 mmol) under argon and stirred at room temperature for 2 h. In a separate flame-dried vial under argon at 0° C., ethyl magnesium bromide in THF (1M, 0.13 mL, 0.13 mmol) was added to a mixture of NiCl$_2$(PPh$_3$)$_2$ (28.8 mg, 0.044 mmol) and PPh$_3$ (25 mg, 0.095 mmol) in Et$_2$O (0.6 mL). The reaction was allowed to stir at 0° C. for 10 min and room temperature for 10 min. A solution of 6-bromo-1-(2-(N,N-diethylamino)ethyl)-1H-indazole (95 mg, 0.32 mmol) in Et$_2$O was added to the catalyst solution by cannula under a positive pressure of argon, along with NMP (2 mL) to rinse vial. The prepared 4-iodozinctetrahydropyran solution was then quickly transferred by cannula under a positive pressure of argon, again using NMP (2 mL) to rinse vial. The septum was replaced with a pressure cap maintaining a steady flow of argon during replacement, and the mixture was heated at 40° C. for 18 h. The mixture was then cooled to room temperature and quenched by adding a saturated aqueous solution of ammonium chloride (5 mL). Once the zinc was completely quenched, the ammonium chloride was neutralized with aqueous sodium bicarbonate (25 mL) and the product was partitioned between 9:1 hexane: dichloromethane (150 mL) and the aqueous phase. The organic extracts were washed sequentially with water (50 mL) and brine (50 mL) and dried over anhydrous sodium sulfate. Flash chromatography (silica gel, 2–5% 2M methanolic ammonia in dichloromethane) yielded an impure product which was further purified by flash chromatography (silica gel, 4% triethylamine in hexane with 0–20% added ethyl acetate) yielding 1-(2-(N,N-diethylamino)ethyl)-6-(tetrahydropyran-4-yl)-1H-indazole (32.6 mg, 34%).

In a like manner, the following additional compounds were prepared:

(b) 1-(2-(N,N-dimethylamino)ethyl)-6-(tetrahydropyran-4-yl)-1H-indazole: (20 mg, 60%); from 4-iodotetrahydropyran (291 mg, 1.37 mmol) and of 6-bromo-1-(2-(N,N-dimethylamino)ethyl)-1H-indazole (32.8 mg, 0.12 mmol). The second flash chromatography was not required in this case.

(c) 1-(2-(N,N-diethylamino)ethyl)-6-(N-Boc-tetrahydro4-pyridinyl)-1H-indazole: (23.7 mg, 90% purity; 60%); from 4-iodo-N-Boc-tetrahydropyridine (309 mg, 0.99 mmol) and of 6-bromo-1-(2-(N,N-diethylamino)ethyl)-1H-indazole (35.3 mg, 0.12 mmol).

(d) 1-(2-(N,N-diethylamino)ethyl)-6-(tetrahydrothiopyran-4-yl)-1H-indazole: (91.3 mg, 46%); from 4-iodotetrahydrothiopyan (309 mg, 0.99 mmol) and of 6-bromo-1-(2-(N,N-diethylamino)ethyl)-1H-indazole (35.3 mg, 0.12 mmol).

Example 17

1-(2-(N,N-diethylamino)ethyl)-6-(N-methyltetrahydro-4-pyridinyl)-1H-indazole A solution of LAH in THF (1M, 0.25 mL, 0.25 mmol) was added to a solution of 1-(2-(N,N-diethylamino)ethyl)-6-(N-Boc-tetrahydro-4-pyridinyl)-1H-indazole (10.2 mg, 0.025 mmol) in THF (0.5 mL) at room temperature under argon and the resulting solution was refluxed for 2 h. After cooling to room temperature, the reaction was quenched using sodium sulfate decahydrate solid and the resulting solid was removed by filtration, extracting the product into ethyl acetate. The solvent was removed in vacuo and purification using an SPE (solid phase extraction) cartridge containing 1 g of silica gel by eluting with 0–10% 2M methanolic ammonia in dichloromethane yielded 1-(2-(N,N-diethylamino)ethyl)-6-(N-methyltetrahydro-4-pyridinyl)-1H-indazole (5.9 mg, 74%).

Example 18

6-(3-Aminopyrrolidin-1-yl)-1-((N,N-dimethylamino)ethyl)-1H-indole

To a mixture of the 6-bromo-1-((N,N-dimethylamino)ethyl)-1H-indole (54 mg, 0.2 mmol), 3-aminopyrrolidine (6 equiv.) and sodium t-butoxide (1.4 equiv.) in xylene was added palladium acetate and $P(t-Bu)_3$ (P/Pd=4). The mixture was heated at 120° C. overnight. The reaction was then poured into ice-cold water followed by extraction with ethyl acetate (2×50 mL). The combined organic extracts were washed with brine, and dried over $Na_2SO_4$ (anhydrous). The organic layer was concentrated in vacuo and purified by flash column chromatography yielding 6-[3-Aminopyrrolidin-1-yl]-1-((N,N-dimethylamino)ethyl)-1H-indole: (43 mg of a yellow oil, 80%).

In a like manner, the following additional compounds were prepared:
(b) 6-(N-morpholinyl)-1-((N,N-dimethylamino)ethyl)-1H-indole: (82 mg of a brown oil, 100%); from 6-bromo-1-(N,N-dimethylaminoethyl)-1H-indole from (80 mg, 0.3 mmol).
(c) 6-(N-thiomorpholinyl)-1-((N,N-dimethylamino)ethyl)-1H-indole: (82 mg of a brown oil, 100%); from 6-bromo-1-(N,N-dimethylaminoethyl)-1H-indole from (80 mg, 0.3 mmol).
(d) 6-(N-morpholinyl)-1-((N,N-dimethylamino)ethyl)-1H-indazole: (2.8 mg, 14%); from 6-bromo-1-(N,N-dimethylaminoethyl)-1H-indazole from (21.0 mg, 0.08 mmol).

Example 19

1-(3-(N,N-dimethylamino)propyl)-6-(3-thienyl)-1H-indazole (i) 1-(3-chloropropyl)-6-(3-thienyl)-1H-indazole 1-chloro-3-iodopropane (0.14 mL, 1.3 mmol) was added to a DMF (3 mL) solution of 6-(3-thienyl)-1H-indazole (88.4 mg, 0.44 mmol) and sodium hydride (60%, 72 mg, 1.8 mmol) that had been allowed to stir for 5 min at room temperature under argon. The reaction mixture was allowed to stir at room temperature overnight before quenching with brine (20 mL) and partitioning into ethyl acetate (100 mL), and drying over anhydrous sodium sulfate. The solvent was removed in vacuo and flash chromatography (silica gel, 10–20% ethyl acetate in hexane) yielded 1-(3-chloropropyl)-6-(3-thienyl)-1H-indazole (76.6 mg, 63%) as well as the side product 2-(3-chloropropyl)-6-(3-thienyl)-2H-indazole (33.9 mg, 28%).

(ii) 1-(3-(N. N-dimethylamino)propyl)-6-(3-thienyl)-1H-indazole

A mixture of 1-(3-chloropropyl)-6-(3-thienyl)-1H-indazole (27.8 mg, 0.10 mmol), potassium iodide (155 mg, 1 mmol), potassium carbonate (130 mg, 1 mmol), and dimethylamine (2M in THF, 0.5 mL, 1 mmol) in acetonitrile (0.5 mL) was heated at reflux overnight. After cooling to room temperature, the mixture was diluted with dichloromethane (5 mL) and filtered through a small plug of alumina to remove the solids, rinsing with dichloromethane (10 mL). After removal of the solvent in vacuo, flash chromatography (silica gel, 2.5–5% 2M methanolic ammonia in dichloromethane) yielded 1-(3-(N,N-dimethylamino)propyl)-6-(3-thienyl)-1H-indazole (27.2 mg, 95%).

In a like manner, the following additional compounds were prepared:
(b) 1-(3-(N,N-diethylamino)propyl)-6-(3-thienyl)-1H-indazole: (26.0 mg, 82%); from 1-(3-chloropropyl)-6-(3-thienyl)-1H-indazole (28.1 mg, 0.10 mmol) and neat diethylamine (0.10 mL, 1 mmol).
(c) 1-(3-(N-pyrrolin-3-yl)propyl)-6-(3-thienyl)-1H-indazole: (20.2 mg, 82%); from 1-(3-chloropropyl)-6-(3-thienyl)-1H-indazole (22.0 mg, 0.08 mmol) and neat 3-pyrroline (250 mg, 3.6 mmol).

Example 20

(R,S)-6-bromo-1-(2-(N,N-dimethylamino)propyl)-1H-indole (i) (R,S)-1-(6-bromo-1H-indol-1-yl)-propan-2-ol A solution of 6-bromo-1H-indole (500 mg, 2.55 mmol) in DMF (4 mL) was added to a suspension of sodium hydride (95%, 77.3 mg, 3.06 mmol) in DMF (4 mL) at room temperature under argon. The mixture was stirred for 30 min prior to cooling in ice-water for the addition of propylene oxide (0.36 mL, 5.1 mmol), and the resulting mixture was stirred at room temperature overnight. After quenching with sodium hydrogen sulfate (aqueous, 1M, 10 mL) the reaction mixture was partitioned between ethyl acetate (100 mL) and water (50 mL). The aqueous layer was extracted using ethyl acetate (2×100 mL) and the combined organic layers were washed sequentially with water (2×100 mL) and brine (150 mL) and dried over anhydrous sodium sulfate. After the solvent was removed in vacuo, flash chromatography (silica gel, 10–20% ethyl acetate in hexane) yielded (R,S)-1-(6-bromo-1H-indol-1-yl)-propan-2-ol (624.8 mg, 96%).

(ii) (R,S)-1-(6-bromo-1H-indol-1-yl)-propan-2-ol methanesulfonate

Methanesulfonyl chloride (0.115 mL, 1.48 mmol) was added to a solution of (R,S)-1-(6-bromo-1H-indol-1-yl)-propan-2-ol ((i), 325 mg, 1.36 mmol) and triethylamine (0.4 mL, 2.9 mmol) in dichloromethane (7 mL) at 0° C. under argon. After stirring for 1 h, the reaction mixture was partitioned between ethyl acetate (200 mL) and brine (20 mL), dried over anhydrous sodium sulfate and the solvent was removed in vacuo to yield (R,S)-1-(6-bromo-1H-indol-1-yl)-propan-2-ol methanesulfonate, which was used crude.

(iii) (R,S)-6-bromo-1-(2-(N,N-dimethylamino)propyl)-1H-indole

A portion of the above methanesulfonate (1.03 mmol) and dimethylamine (40% aqueous, 1.8 mL) in DMF (3.6 mL) under argon was heated at 65° C. for 4 days under argon. After cooling to room temperature, the product was partitioned between ethyl acetate (200 mL) and water (40 mL), and the organic layer was washed sequentially with water (3×40 mL) and brine (40 mL), and dried over anhydrous sodium sulfate. Flash chromatography (silica gel, 1–3% 2M methanolic ammonia in dichloromethane) yielded (R,S)-6-bromo-1-(2-(N,N-dimethylamino)propyl)-1H-indole (193 mg, 67%).

Example 21

(R)-1-(N-methylpyrrolidin-2-yl)methyl)-6-(3-thienyl)-1H-indazole (i) (R)-1-(N-Boc-pyrrolidin-2-yl)methyl)-6-(3-thienyl)-1H-indazole Methanesulfonyl chloride (0.06 mL, 0.77 mmol) was added to a solution of (R)-N-Boc-pyrrolidine-2-methanol (125.3 mg, 0.62 mmol) and triethylamine (0.22 mL, 1.6 mmol) in dichloromethane at 0° C. under argon. After stirring for 1 h, the reaction mixture was partitioned between dichloromethane (50 mL) and sodium hydrogen sulfate (15 mL). The organic layer was sequentially washed with water (15 mL) and brine (15 mL), dried over anhydrous sodium sulfate and the solvent was removed in vacuo to yield (R)-N-Boc-pyrrolidine-2-methanol methanesulfonate, which was used crude.

DMF was added at 0° C. to a mixture of 6-(3-thienyl)-1H-indazole (62 mg, 0.31 mmol) and sodium hydride (60%, 50 mg, 1.25 mmol) under argon and the resulting mixture was stirred for 1 h. The crude (R)-N-Boc-pyrrolidine-2-methanol methanesulfonate was added as a solution in DMF (1.0 mL, divided with part reserved to rinse vial and cannula). The resulting mixture was allowed to stir at room temperature overnight, and heated at 90° C. for 1 h to complete the reaction. After cooling to room temperature, the reaction was quenched with water (10 mL) and brine (10 mL) and extracted into ethyl acetate (100 mL). The organic layer was washed with brine (2×15 mL) and dried over anhydrous sodium sulfate, and the solvent was removed in vacuo. Flash chromatography (silica gel, 20–40% ethyl acetate in hexane) yielded (R)-1-(N-Boc-pyrrolidin-2-yl)methyl)-6-(3-thienyl)-1H-indazole (69.1 mg, 58%) as well as the isomer, (R)-2-(N-Boc-pyrrolidin-2-yl)methyl)-6-(3-thienyl)-2H-indazole (69.9 mg, 50% purity, 29%).

In a like manner, the following additional compounds were prepared:

(b) (R)-6-Bromo-1-((N-methylpyrrolidin-2-yl)methyl)-1H-indole: (208 mg, 35%); from 6-bromo-1H-indole (398.1 mg, 2.03 mmol) and (R)-N-methylpyrrolidine-2-methanol (via the methanesulfonate, 467.8 mg, 4.06 mmol).

(c) (S)-6-Bromo-1-((N-methylpyrrolidin-2-yl)methyl)-1H-indole: (110 mg, 15%); from 6-bromo-1H-indole (500 mg, 2.55 mmol) and (S)-N-methylpyrrolidine-2-methanol (via the methanesulfonate, 0.51 mL, 5.1 mmol).

Example 22

(R)-1-(N -methyl pyrrolidin-2-yl)methyl)-6-(3-thienyl)-1H-indazole

LAH (1M in THF, 0.36 mL, 0.36 mmol) was added to a solution of (R)-1-(N-Boc-pyrrolidin-2-yl)methyl)-6-(3-thienyl)-1H-indazole (35 mg, 0.091 mmol) in THF (1.0 mL) and the resulting solution was heated at reflux overnight. After cooling to room temperature, the reaction was quenched using sodium sulfate decahydrate solid and the resulting solid was removed by filtration, extracting the product into ethyl acetate. The solvent was removed in vacuo and flash chromatography (silica gel, 2–3.5% 2M methanolic ammonia in dichloromethane yielded (R)-1-(N-methylpyrrolidin-2-yl)methyl)-6-(3-thienyl)-1H-indazole (22.7 mg, 84%).

Example 23

(R)-1-(pyrrolidin-2-yl)methyl)-6-(3-thienyl)-1H-indazole

A solution of hydrochloric acid (3M in ethyl acetate, 0.7 mL, 2.1 mmol) was added to (R)-1-(N-Boc-pyrrolidin-2-yl)methyl)-6-(3-thienyl)-1H-indazole (35 mg, 0.091 mmol) at room temperature. The resulting solution was stirred for 30 min prior to quenching with sodium hydroxide (4N aqueous, 0.8 mL, 3.2 mmol) and extraction using a VARIAN EX-TUBE (3 mL, eluting with ethyl acetate 10 mL). The solvent was removed in vacuo and flash chromatography (silica gel, 5–7.5% 2M methanolic ammonia in dichloromethane) yielded (R)-1-(pyrrolidin-2-yl)methyl)-6-(3-thienyl)-1H-indazole (19.6 mg, 76%).

Example 24

(R)-6-(4-hydroxy-N-methylpiperidin-4-yl)-1-(N-methylpyrrolidin-2-yl)methyl)-1H-indole n-Butyllithium (2.5M in hexane, 0.26 mL, 0.65 mmol) was added to a solution of (R)-6-bromo-1-(N-methylpyrrolidin-2-yl)methyl)-1H-indole (77.5 mg, 0.26 mmol) in THF (mL) at −78° C. and the resulting solution was stirred for 1 h prior to the addition of 1-methyl-4-piperidone (0.08 mL, 0.65 mmol). After stirring the mixture for 30 min, the reaction was warmed to room temperature for 30 min and quenched with pH 7 phosphate buffer (2 mL). The product was partitioned between ethyl acetate (100 mL) and water (20 mL). The organic layer was washed with water (20 mL) and brine (20 mL) and dried over anhydrous sodium sulfate. The solvent was removed in vacuo and purification using an SPE tube (silica, 1 g, eluting with 0–15% 2M methanolic ammonia in dichloromethane) yielded (R)-6-(4-hydroxy-N-methylpiperidin4-yl)-1-(N-methylpyrrolidin-2-yl)methyl)-1H-indole (59.6 mg, 69%).

Example 25

(R)-1-(N-methylpyrrolidin-2-yl)methyl)-6-(1-methyl-1,2,5,6-tetrahydro-4-pyridine)-1H-indole Trifluoroacetic acid (1 mL) was added to a solution of (R)-6-(4-hydroxy-N-methylpiperidin-4-yl)-1-(N-methylpyrrolidin-2-yl)methyl)-1H-indole (58 mg, 0.18 mmol) in THF (4 mL) and the solution was heated at reflux for 45 min and then left at room temperature overnight (still incomplete). The reaction mixture was partitioned between dichloromethane (50 mL) and sodium hydroxide (25 mL), and the organic layer was washed with water (25 mL) and brine (25 mL), dried over anhydrous sodium sulfate and the solvent was removed in vacuo. Flash chromatography yielded (R)-1-(N-methylpyrrolidin-2-yl)methyl)-6-(1-methyl-1,2,5,6-tetrahydro-4-pyridine)-1H-indole (10 mg, 18%) as well as recovered starting material (10 mg, 17%).

Example 26

(R)-6-(N-methylpiperidin4-yl)-1-(N-methylpyrrolidin-2-yl)methyl)-1H-indole

A small scoop of palladium on carbon (10%, approx. 10 mg, catalytic) was added to a solution of (R)-1-(N-methylpyrrolidin-2-yl)methyl)-6-(1-methyl-1,2,5,6-tetrahydro-4-pyridine)-1H-indole (8.5 mg, 0.027 mmol) in methanol (1 mL). The resulting mixture was stirred under an atmosphere of hydrogen gas in a balloon for 24 h. The catalyst was removed by filtration through an SPE cartridge (silica, 1 g, washed first with methanol, then eluted compound with 10% 2M methanolic ammonia in dichloromethane) to yield (R)-6-(N-methylpiperidin4-yl)-1-(N-methylpyrrolidin-2-yl)methyl)-1H-indole (6.4 mg, 75%).

Example 27

6-Iodo-1H-indazole

Sodium nitrite (5.87 g, 85 mmol) in water (20 mL) was added dropwise to an ice-cooled solution of 6-aminoindazole (10 g, 75.6 mmol) in DMF (80 mL) and hydrochloric acid (6M, 40 mL) and the mixture was stirred for 30 minutes. Potassium iodide (13.5 g) was then added in small portions (gas evolution occurred) and the mixture was stirred for 1 h before warming to room temperature for 16 h. The reaction was neutralized with aqueous sodium bisulfite followed by aqueous sodium hydroxide. The mixture was filtered to remove solid, and the solid was washed first with water to remove impurities, and then with ethyl acetate and THF to collect the product. The organic washes were evaporated and recombined with the aqueous layer for extraction with ethyl acetate (3×250 mL). The organic layer was washed sequentially with water and brine, dried over sodium sulfate, and the solvent was removed in vacuo. Filtration chromatography on silica gel (35–60% ethyl acetate in hexane) yield a yellow solid, which was then triturated with 50% ethyl acetate in hexane and finally ethyl acetate to yield the product (4.96 g).

Example 28

General Procedure for Salt Formation

Hydrochloric acid salt: acid (1 to 4mol. equiv., 1M in diethyl ether) is added to a solution of the substrate (1 mol. equiv.) in dichloromethane (approx. 0.1 M solution) and the mixture is stirred for 5 to 20 min. The solvent and excess acid are removed in vacuo and the crude product is recrystallized from methanol—ether.

Other salts: The appropriate acid (1 to 2mol. equiv. solid acids; or 0.5 to 1 mol equiv. of a diacid) is added to a solution of the substrate (1 mol. equiv.) in methanol (0.14 M solution) and the mixture stirred overnight. The solvent is removed in vacuo and the crude product purified.

Example 29

Comparison of the Binding Affinities

Selected compounds of the previous examples, as well as reference compounds, were evaluated for binding affinity using cell types receptive specifically to 5-$HT_{1D}$ and 5-$HT_{1B}$ ligands. The assay protocol generally entailed the incubation of membranes prepared from cells expressing the 5-$HT_{1D}$ or 5-$HT_{1B}$ subtype of 5-HT receptors with $^3$H-serotonin (1 nM for 5-$HT_{1D}$ and 2.5 nM for 5-$HT_{1B}$). Specific concentrations of the test compound were incubated with the radioligand and the membrane homogenates prepared from the recombinant cells. After a 60 minute incubation at 22° C., the incubation was terminated by vacuum filtration. The filters were washed with buffer and counted for radioactivity using liquid scintillation spectroscopy. The affinity of the test compound for the 5-$HT_{1D}$ receptor is expressed as the amount (in percent) of binding of the radioligand that is inhibited in the presence of 100 nM of test compound. A greater percent inhibition indicates greater affinity for the 5-$HT_{1D}$ receptor. Preferred compounds of the invention, for example those of examples 3f, 9g, 10o, 10p, 12b, 13 and 25 showed a percent inhibition of greater than 50% at the 5-$HT_{1D}$ receptor. More preferred compounds of the invention, for example those of examples 5e, 10t, 10dd and 16 showed a percent inhibition of greater than 75% at the 5-$HT_{1D}$ receptor. Most preferred compounds of the invention, for example those of examples 6, 8, 10b, 10w, 19c and 21 showed a percent inhibition of greater than 90% at the 5-$HT_{1D}$ receptor.

In terms of selectivity, preferred compounds of the invention, for example those of examples 10, 21 and 23 having a percent inhibition of greater than 75% at the 5-$HT_{1D}$ receptor also had a percent inhibition of less than 50% at the 5-$HT_{1B}$ receptor. More preferred compounds, for example those of examples 5, 5e, 6, 8, 9p, 10q, 10t, 12, 16d and 21 showed a percent inhibition of greater than 75% at the 5-$HT_{1D}$ receptor and a percent inhibition of less 25% at the 5-$HT_{1B}$ receptor. Most preferred compounds, for example those of examples 3, 5e, 9b, 9i, 10h, 10i, 16 and 19c showed a percent inhibition of greater than 75% at the 5-$HT_{1D}$ receptor and a percent inhibition of less 15% at the 5-$HT_{1B}$, receptor.

Example 30

Functional Assays

The 5$HT_{1D}$ and 5$HT_{1B}$ receptor subtypes respond to serotonin and other agonists by reducing adenyl cyclase mediated production of cyclic AMP. Particular test compounds were assayed for their ability to inhibit adenyl cyclase activity using the procedure described below. Forskolin was used to elevate the basal adenyl cyclase activity.

Compounds acting as antagonists at the 5$HT_{1D}$ and 5$HT_{1B}$ receptor subtypes will antagonize the agonist effect of serotonin and thus, will block the serotonin-induced inhibition of forskolin-stimulated adenyl cyclase activity.

CHO Pro 5 cells stably expressing either the human 5$HT_{1D}$ or human 5$HT_{1B}$ receptors were plated in 6 well plates in DMEM (Dulbecco's Modified Eagle Medium)/F12 (Nutrient Mixture F12—Ham) media with 10% FCS (fetal calf serum) and G418 (Geneticen Disulfate, 500 ug/mL), and incubated at 37° C. in a $CO_2$ incubator. The cells were allowed to grow to about 70% confluence before use in the assay.

The culture media of each well was removed, and the wells were washed once with serum free media. Then 2 mL of SFM+IBMX medium (SFM with 0.5 mM IBMX, 3-isobutyl-1-methylxanthine, 0.1% ascorbic acid and 10 mM pargyline) was added to each well and the wells were incubated at 37° C. for 10 min. Following incubation, the SFM+IBMX media was removed from each well and fresh SFM+IBMX media was added to the wells separately with one of a) forskolin (10 mM final concentration); b) serotonin and forskolin (both 10 mM final concentration); c) test compound (100 nM and 10 $\mu$M) and forskolin (10 mM final concentration) (to test for agonist activity); and d) test compound (100 nM and 10 $\mu$M) along with serotonin and forskolin (both 10 mM final concentration) (to test for antagonist activity). Basal adenyl cyclase activity was determined from wells with only SFM+IBMX media added.

The cells were then incubated at 37° C. for 30 minutes in a $CO_2$ incubator. Following incubation, the media were removed from each well. The wells were washed once with 1 mL of PBS (phosphate buffered saline). Each well was then treated with 1 mL cold 95% ethanol:5 mM EDTA (2:1) at 4° C. for 1 hour. The cells from each well were then scraped and transferred into individual Eppendorf tubes. The tubes were centrifuged for 5 minutes at 4° C., and the supernatants were transferred to new Eppendorf tubes. The pellets were discarded and the supernatants were stored at 4° C. until assayed for cAMP concentration. cAMP content for each extract was determined in duplicate by EIA (enzyme-immunoassay) using the Amersham Biotrak cAMP EIA kit (Amersham RPN 225).

Total inhibition ($I_o$) of forskolin-stimulated adenyl cyclase activity by serotonin was determined as the difference in concentration of cAMP in the forskolin-treated cells ($C_f$) and serotonin-forskolin treated cells ($C_d$).

$$I_o = C_f - C_d$$

Likewise, inhibition of forskolin-stimulated adenyl cyclase activity by an agonist test compound was determined as the difference in concentration of cAMP in the forskolin-treated cells and test compound-forskolin treated cells. Agonist activity is expressed as % forskolin response.

Net inhibition (I) of forskolin-stimulated adenyl cyclase activity by serotonin in the presence of an antagonist was determined as the difference in concentration of cAMP in the forskolin-treated cells ($C_f$) and cAMP concentrations in test compound, serotonin and forskolin-treated cells (C).

$$I = C_f - C$$

The ability of the test compounds to reverse the serotonin inhibition of forskolin-stimulated adenyl cyclase activity (% reversal, % R) was determined by the formula:

$$\% R = (1 - I/I_o) \times 100$$

Compounds of the invention caused a decrease in the forskolin stimulated production of cAMP in CHO cells stably expressing the $5\text{-HT}_{1D}$ receptor, at concentrations of 100 nM and 10 µM, and therefore act as agonists at this receptor.

Example 31

Pharmaceutical Examples

Tablets

These may be prepared by the normal methods such as wet granulation or direct compression.

A. Direct Compression

|  | mg/tablet |
|---|---|
| Active ingredient | 10.0 |
| Microcrystalline Cellulose USP | 188.5 |
| Magnesium Stearate BP | 1.5 |
| Total weight | 200.0 |

The active ingredient is sieved through a suitable sieve, blended with the excipients and compressed using 7 mm diameter punches. Tablets of other strengths may be prepared by altering the compression weight and using punches to suit.

B. Wet Granulation

|  | mg/tablet |
|---|---|
| Active ingredient | 10.0 |
| Lactose BP | 143.5 |
| Starch BP | 30.0 |
| Pregelatinised Maize Starch BP | 15.0 |
| Magnesium Stearate BP | 1.5 |
| Total weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

C. For Buccal Administration

|  | mg/tablet |
|---|---|
| Active ingredient | 10.0 |
| Lactose BP | 86.8 |
| Sucrose BP | 86.7 |
| Hydroxypropyl methylcellulose | 15.0 |
| Magnesium Stearate BP | 1.5 |
| Total weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film-coated with suitable film-forming materials, such as hydroxypropyl methylcellulose, using standard techniques. Alternatively the tablets may be sugar coated.

Capsules

|  | mg/capsule |
|---|---|
| Active ingredient | 10.0 |
| *Starch 1500 | 89.0 |
| Magnesium Stearate BP | 1.0 |
| Fill Weight | 100.0 |

*A form of directly compressible starch

The active ingredient is sieved and blended with the excipients. The mix is filled into size No. 2 hard gelatin capsules using suitable machinery. Other doses may be prepared by altering the fill weight and if necessary changing the capsule size to suit.

Syrup

|  | mg/5 mL dose |
|---|---|
| Active ingredient | 10.0 |
| Sucrose BP | 2750.0 |
| Glycerine BP | 500.0 |
| Buffer | as required |
| Flavour | as required |
| Colour | as required |
| Preservative | as required |
| Distilled water | to 5.0 mL |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup produced is clarified by filtration.

| Suppositories | |
|---|---|
| Active ingredient | 10.0 mg |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

| Injection for Intravenous Administration | |
|---|---|
| | % w/v |
| Active ingredient | 0.2 |
| Sodium Chloride BP | as required |
| Water for Injection BP | to 100.00 |

Sodium chloride may be added to adjust the tonicity of the solution and the pH may be adjusted, using acid or alkali, to that of optimum stability and/or to facilitate solution of the active ingredient. Alternatively suitable buffer salts may be used. The solution is prepared, clarified and filled into appropriate size ampoules sealed by fusion of the glass. The injection is sterilized by heating in an autoclave using one of the acceptable cycles. Alternatively the solution may be sterilized by filtration and filled into sterile ampoules under aseptic conditions.

The solution may be packed under an inert atmosphere of nitrogen or other suitable gas.

| Inhalation Cartridges | |
|---|---|
| | mg/cartridge |
| Active ingredient micronised | 1.0 |
| Lactose BP | 39.0 |

The active ingredient is micronised (Microniser is a Registered Trade Mark) in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo

| Metered Dose Pressurized Aerosol | | |
|---|---|---|
| | mg/metered dose | per can |
| Active ingredient, micronised | 0.50 | 120.0 mg |
| Oleic Acid BP | 0.05 | 12.0 mg |
| Trichlorofluoromethane BP | 22.25 | 5.34 g |
| Dichlorofluoromethane BP | 62.2 | 14.92 g |

The active ingredient is micronised in a fluid energy mill to a fine particle size range. The oleic acid is mixed with the trichlorofluoromethane at a temperature of 10–15° C. and the pulverized drug is mixed into the solution with a high shear mixer. The suspension is metered into aluminum aerosol cans and suitable metering valves, delivering a metered amount of 85 mg of suspension, are crimped onto the cans and the dichlorodifluoromethane is pressure filled into the cans through the valves.

We claim:

1. A compound selected from the group consisting of a compound of Formula II:

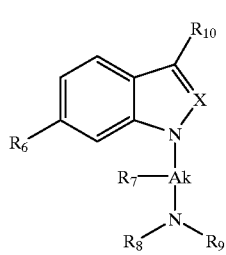

wherein:
X is CH;
$R_6$ represents a 6-membered monocyclic or benzo-fused heterocyclic ring, which is optionally unsaturated, and which optionally contains one or more substituents selected from the group consisting of lower alkyl, hydroxy, lower alkoxy, amino and mono- or di-lower alkyl amino;
Ak represents a $C_{1-3}$ alkylene chain which which optionally is substituted with $R_7$, where $R_7$ represents lower alkyl;
$R_8$ and $R_9$ are independently selected from the group consisting of H, lower alkyl, lower alkenyl, cycloalkyl and optionally-substituted benzyl;
$R_{10}$ is selected from the group consisting of H, lower alkyl and a 6-membered monocyclic or bicyclic group with one sulfur atom, which optionally is saturated or unsaturated, and optionally contains one or more substituents selected from the group consisting of lower alkyl, hydroxy, lower alkoxy, amino and mono or di lower alkylamino;
and a salt, solvate or prodrug thereof.

2. A composition comprising a compound according to claim 1 and a carrier.

3. A composition comprising a compound according to claim 1, in an amount effective to stimulate a 5-HT$_{1D}$ receptor, and a pharmaceutically acceptable carrier.

4. A compound selected from the group consisting of:
1-(2-(N,N-Diethylamino)ethyl 6-(2,3-dihydrothiopyran-4y)-1H-indole;
1-(2-(N,N-Diethylamino)ethyl)6-(4-hydroxy-tetrahydrothiopyran-4-yl)-1H-indole;
1-(2-(N,N-Diethylamino)ethyl)-6-(tetrahydrothiopyran-4-yl)-1H-indole;
1-(2-(N,N-Dimethylamino)ethyl)-6-(4-hydroxy-tetrahydrothiopyran-4-yl)-1H-indole;
1-(2-(N,N-Dimethylamino)ethyl)-6-(tetrahydrothiopyran-4-yl))-1H-indole;
1-(3-(N,N-Dimethylamino)propyl)6-(4-hydroxy-tetrahydrothiopyran-4-yl)-1H-indole;
1-(3-(N,N-Dimethylamino)propyl)-6-(tetrahydrothiopyran-4-yl)-1H-indole;
1(N-Cyclopropylamino)ethyl)-6-(4-hydroxytetrahydrothlopyran-4-yl)-1H-indole;
1(N-Cyclopropylaminozethyl-6-(2,3-dihydrothiopyran-4-yl)-1H-indole;
6-(6H-2,3-Dihydrothiopyran-4-yl)-1-(2-(N,N-dimethylamino)ethyl)-1H-indole;

6-(6H-2,3-Dihydrothiopyran-4-yl)-(3-(N,N-dimethylamino)propyl)-1H-indole.

5. A compound selected from the group consisting of:

1-((N-Cyclopropylamino)ethyl)-6-(2,3-dihydrothiopyran-4-yl)-1H-indole;

1-(2-(N,N-Diethylamino)ethyl)-6-(2,3-dihydrothiopyran-4-yl)-1H-indole;

1-(2-(N,N-Diethylamino)ethyl)-6-(4-hydroxy-tetrahydrothiopyran-4-yl)-1H-indole;

1-(2-(N,N-Diethylamino)ethyl)-6-(tetrahydrothiopyran-4-yl)-1H-indazole;

1-(2-(N,N-Diethylamino)ethyl)-6-(tetrahydrothiopyran-4-yl)-1H-indole;

1-(2-(N,N-Diethylamino)ethyl)-6-(4-hydroxy-tetrahydrothiopyran-4-yl)-1H-indole;

1-(2-(N,N-Diethylamino)ethyl)-6-(tetrahydrothiopyran-4-yl)-1H-indole;

1-(N-Cyclopropylamino)ethyl)-6-(4-hydroxy-tetrahydrothiopyran-4-yl)-1H-indole.

6. A compound of claim 1 wherein $R_{10}$ is selected from the group consisting of H and lower alkyl.

7. A compound of claim 6 wherein $R_{10}$ is H.

8. A compound of claim 1 wherein $R_8$ and $R_9$ are selected from the group consisting of H, lower alkyl and cycloalkyl.

\* \* \* \* \*

UNITED STATES PATENT AND TRADEMARK OFFICE
CERTIFICATE OF CORRECTION

PATENT NO. : 6,380,242 B1
DATED : April 30, 2002
INVENTOR(S) : Arora et al.

It is certified that error appears in the above-identified patent and that said Letters Patent is hereby corrected as shown below:

Column 42,
Lines 21-22, after "benzo-fused heterocyclic ring" insert -- containing sulfur atom --

Signed and Sealed this

Twenty-first Day of January, 2003

JAMES E. ROGAN
*Director of the United States Patent and Trademark Office*